(12) United States Patent
Kothapalli et al.

(10) Patent No.: US 7,653,232 B2
(45) Date of Patent: Jan. 26, 2010

(54) PHASE BASED DIGITAL IMAGING

(75) Inventors: Sri-Rajasekhar Kothapalli, St. Louis, MO (US); Chandra S. Yelleswarapu, Dorchester, MA (US); Pengfei Wu, Malden, MA (US); D. V. Gopal L. N. Rao, Lexington, MA (US)

(73) Assignee: University of Massachusetts, Boston, MA (US)

( * ) Notice: Subject to any disclaimer, the term of this patent is extended or adjusted under 35 U.S.C. 154(b) by 519 days.

(21) Appl. No.: 11/342,254

(22) Filed: Jan. 27, 2006

(65) Prior Publication Data

US 2006/0291707 A1 Dec. 28, 2006

Related U.S. Application Data

(60) Provisional application No. 60/648,637, filed on Jan. 28, 2005.

(51) Int. Cl.
*G06K 9/00* (2006.01)
*A61B 6/04* (2006.01)

(52) U.S. Cl. .................................................... 382/132
(58) Field of Classification Search ................ 382/128, 382/129, 130, 131, 132, 133, 134, 280, 190, 382/254, 266; 378/98, 37, 46, 62, 90, 92, 378/98.4, 101, 901; 324/307; 600/407, 410, 600/425; 128/920, 922, 915; 250/339.08
See application file for complete search history.

(56) References Cited

U.S. PATENT DOCUMENTS

| | | | | |
|---|---|---|---|---|
| 5,352,979 A | * | 10/1994 | Conturo | 324/307 |
| 5,825,846 A | * | 10/1998 | Aach et al. | 378/98 |
| 6,219,571 B1 | * | 4/2001 | Hargreaves et al. | 600/410 |
| 6,970,587 B1 | * | 11/2005 | Rogers | 382/132 |

* cited by examiner

*Primary Examiner*—Abolfazl Tabatabai
(74) *Attorney, Agent, or Firm*—Wilmer Cutler Pickering Hale & Dorr LLP.

(57) ABSTRACT

The present invention relates to systems and methods for medical imaging. Digital images are processed to provide phase images of a region of interest to aid in the diagnosis and treatment of various conditions. A preferred embodiment of the invention provides improved mammography screening for cancerous or precancerous conditions.

24 Claims, 41 Drawing Sheets

Phase only image reconstruction algorithm.

Phase only image reconstruction algorithm.

Reconstructed Phase-only Image
With Edge Enhancement

Original Image

Reconstructed phase only image making simulated microcalcifications visible to the naked eye.

Digital Phantom with simulated microcalcifications not visible to the naked eye.

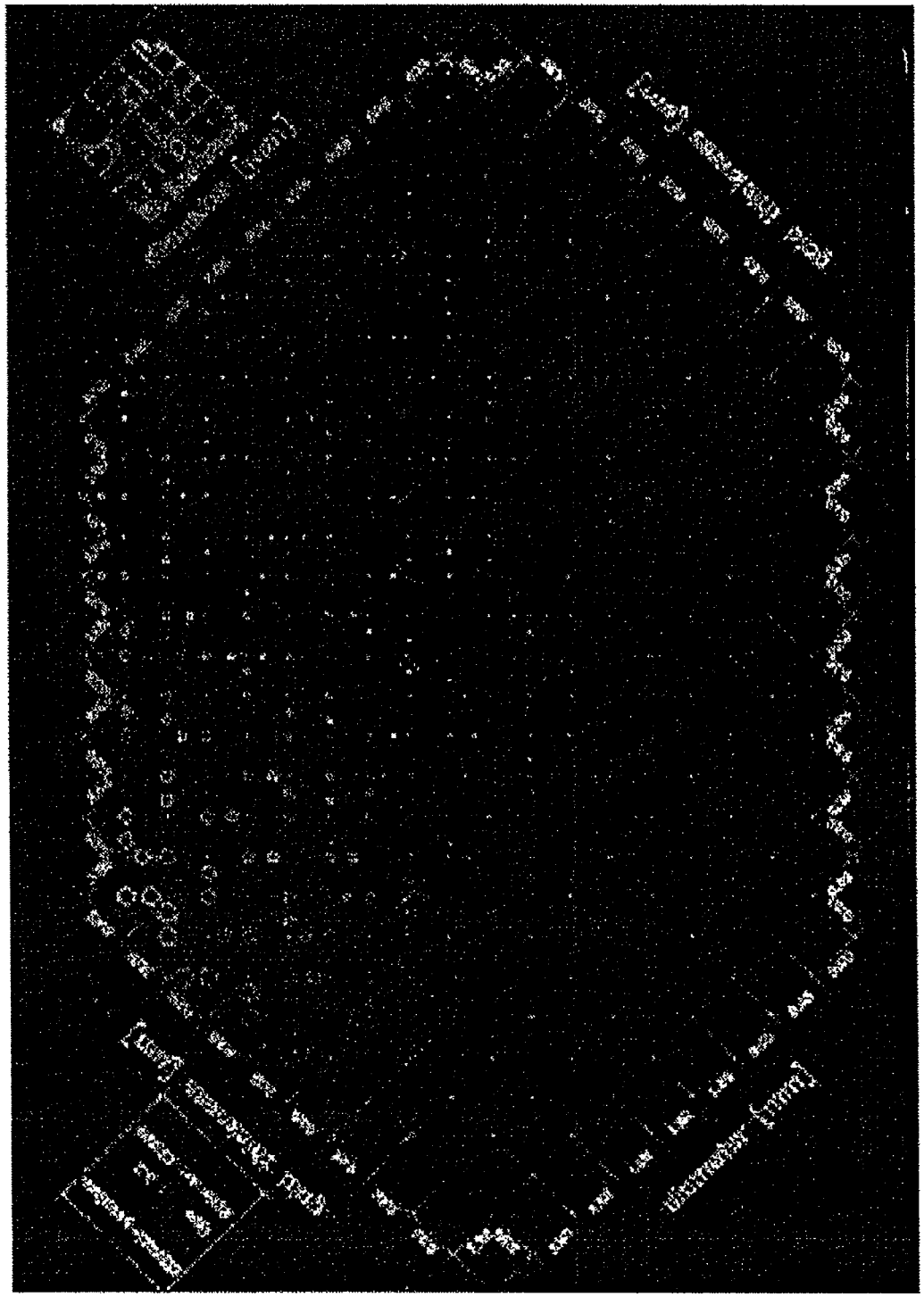

FIG. 5C Respective Contrast Adjusted Phase-only Image
FIG. 5B Phase-only Image
FIG. 5A Original Mammogram

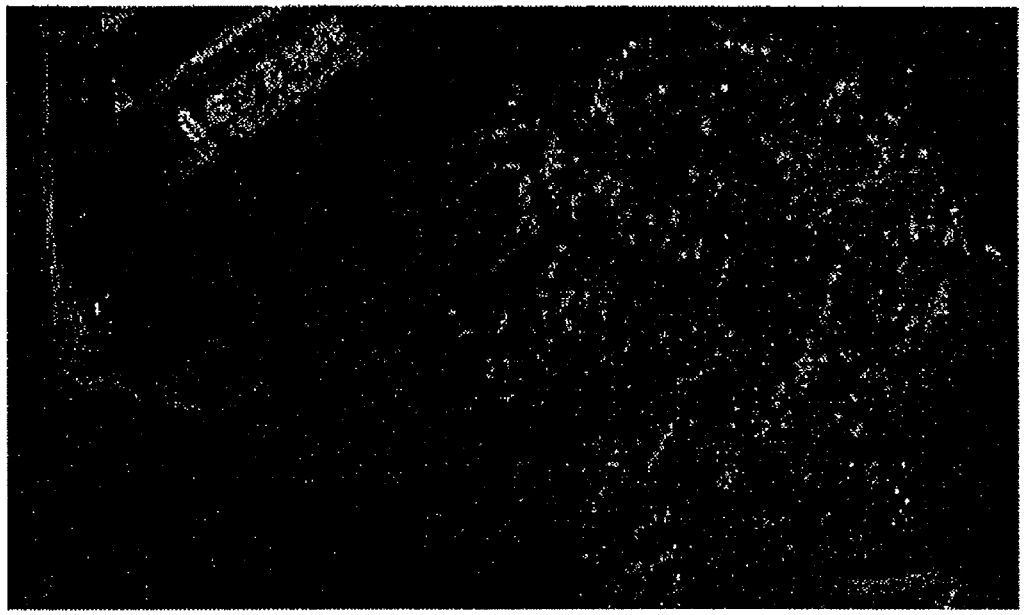
FIG. 6B Phase-only Image
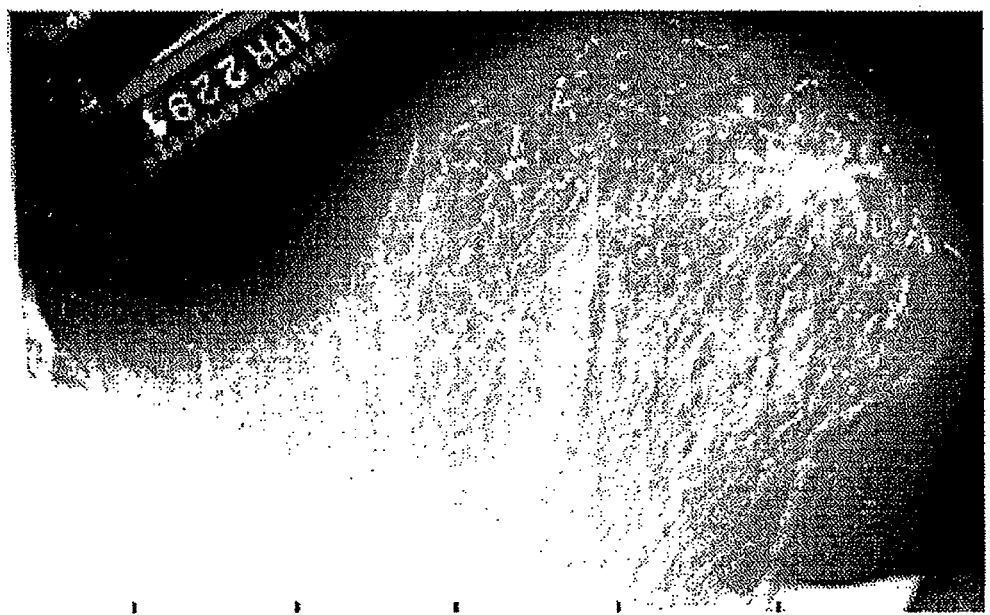
FIG. 6A Original Mammogram

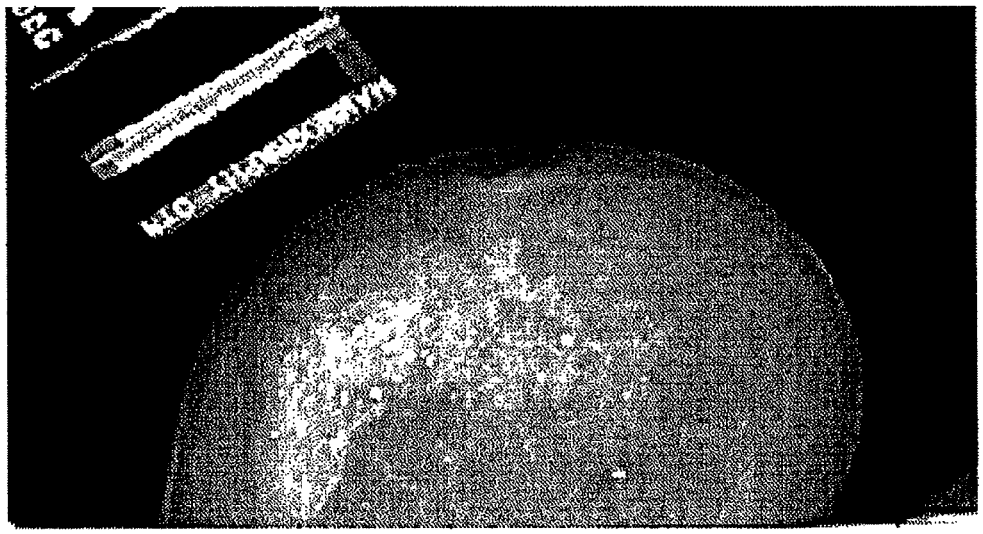
FIG. 7A Original Mammogram
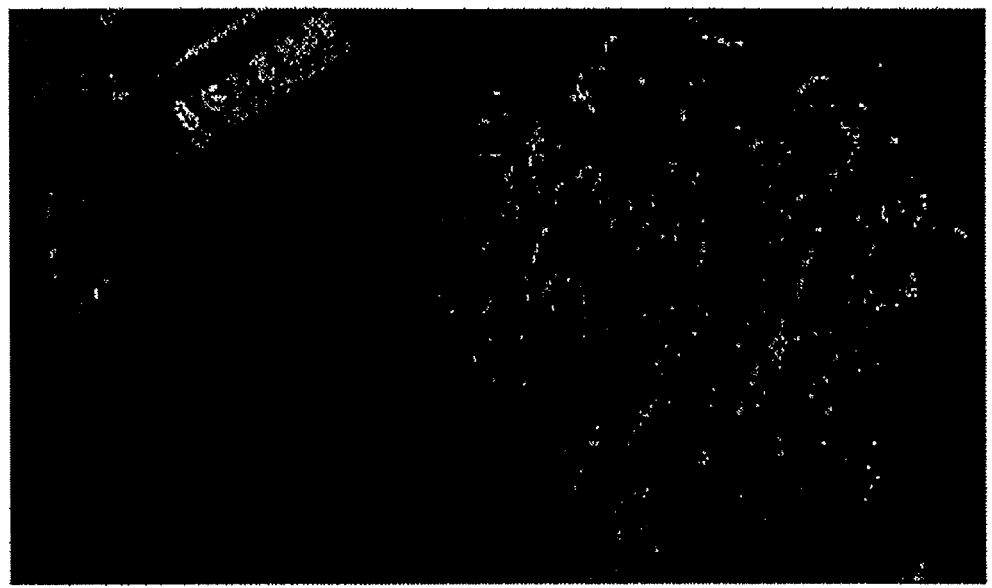
FIG. 6C Respective Contrast Adjusted Phase-only Image

FIG. 7C  Respective Contrast Adjusted Phase-only Image
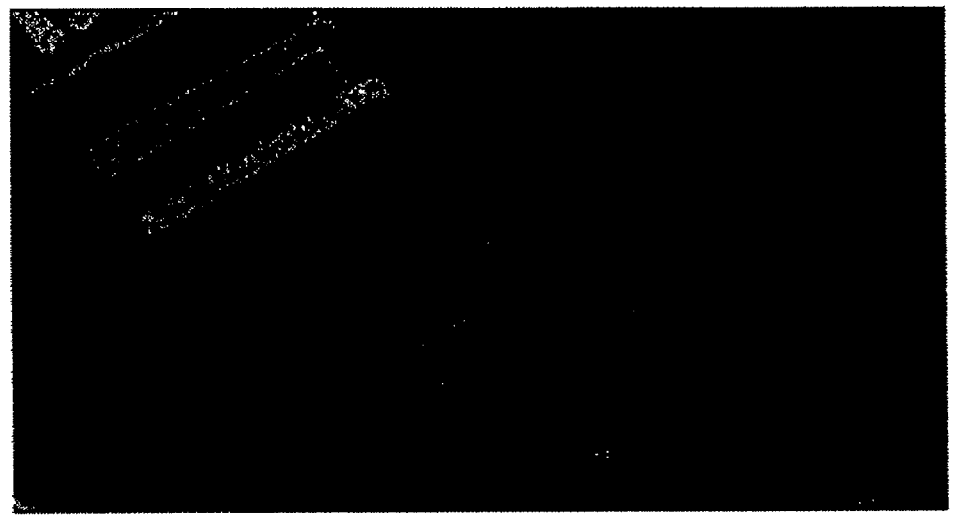
FIG. 7B  Phase-only Image

FIG. 8B  Phase-only Image
FIG. 8A  Original Mammogram

Respective Contrast Adjusted Phase-only Image

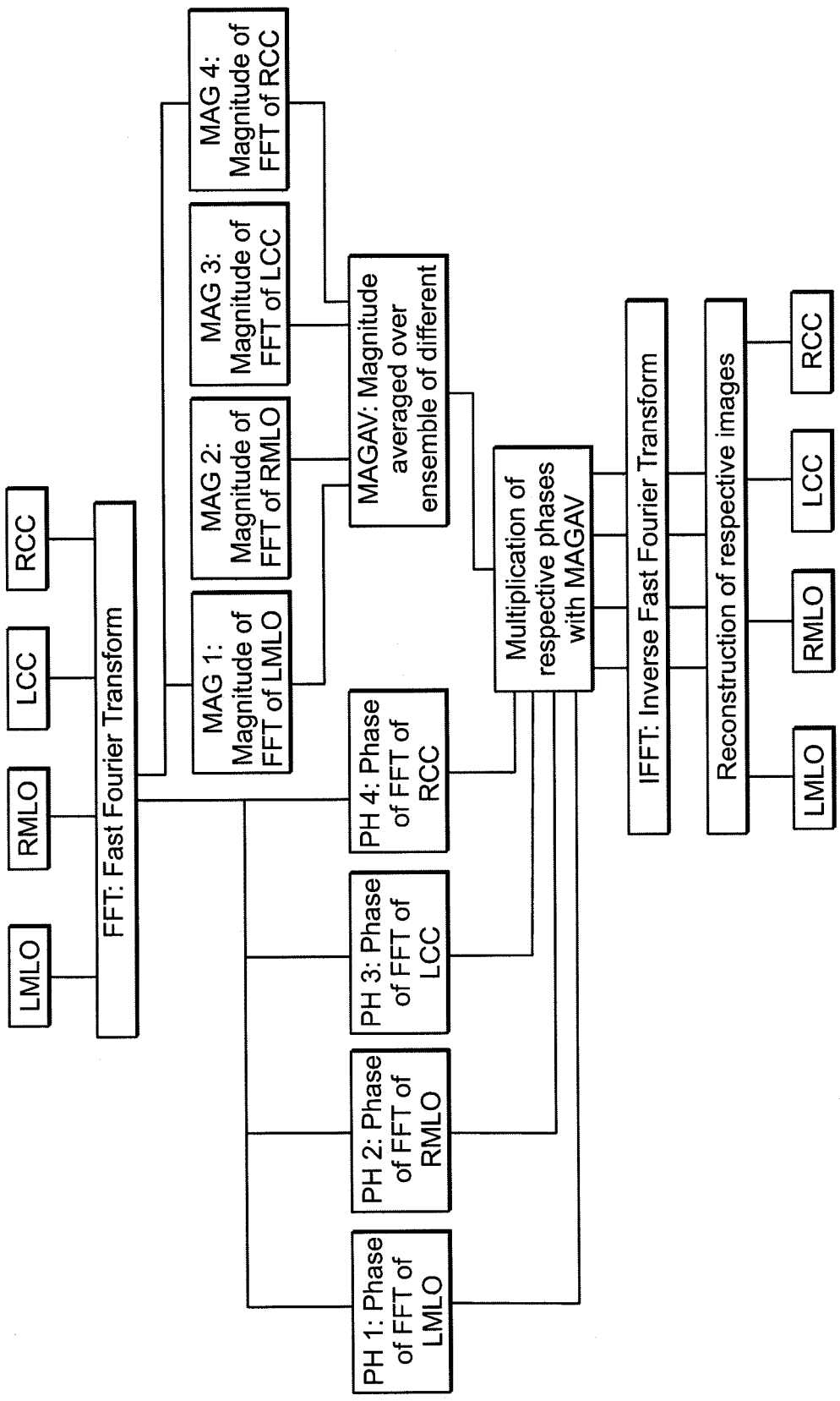
FIG. 9  An algorithm for original image reconstruction from its phase only information Reconstruction of original mammogram from its phase and the magnitude of FIG. 11A Original digital mammogram: RMLO view Phase only image reconstruction of FIG 10A Reconstruction of original mammogram from its phase and the averaged magnitude of FIG. 10A and FIG. 11A

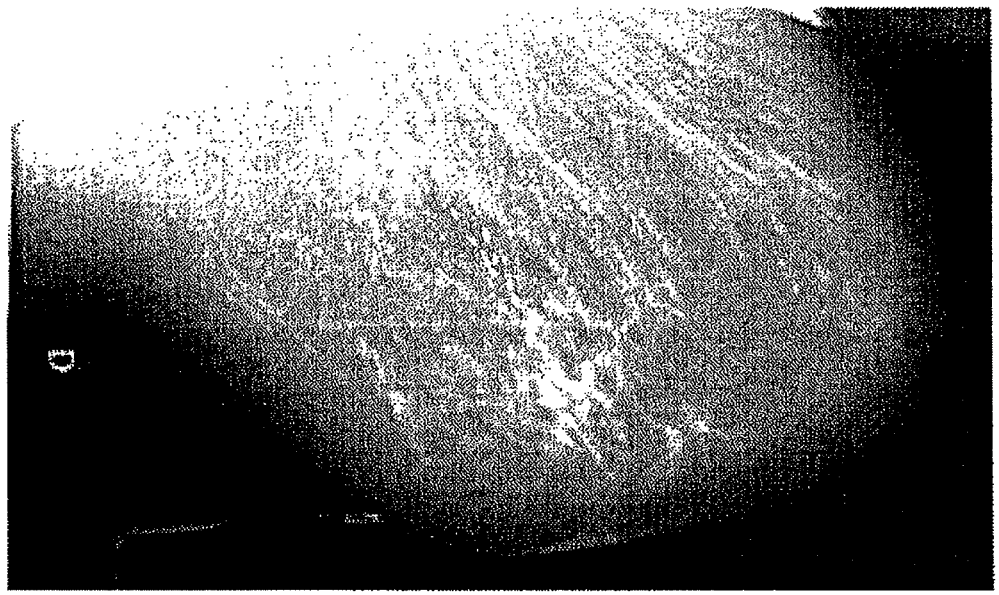
FIG. 11A  Original digital mammogram: LMLO view
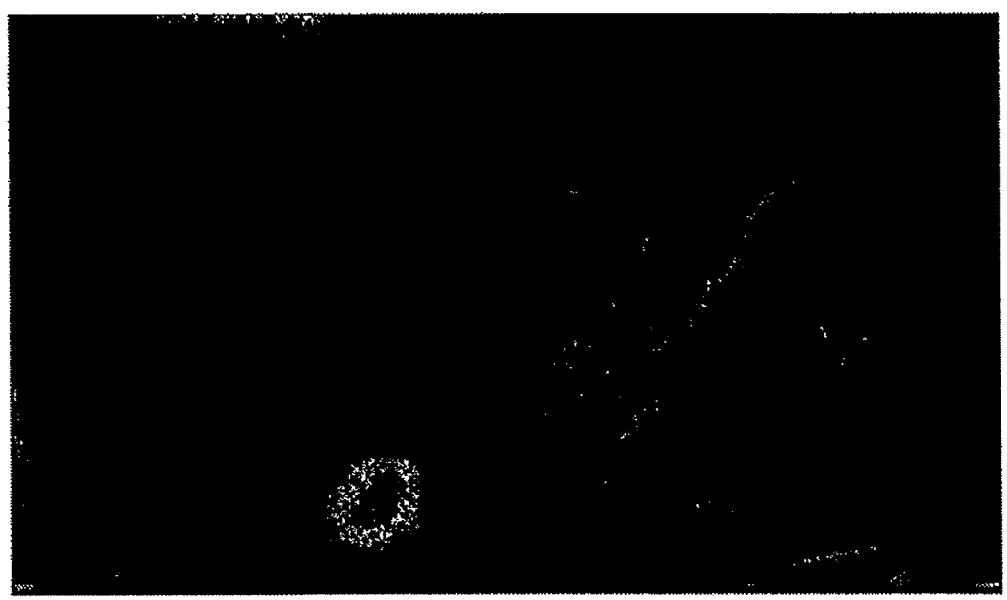
FIG. 10E  Contrast adjusted image of FIG 10D

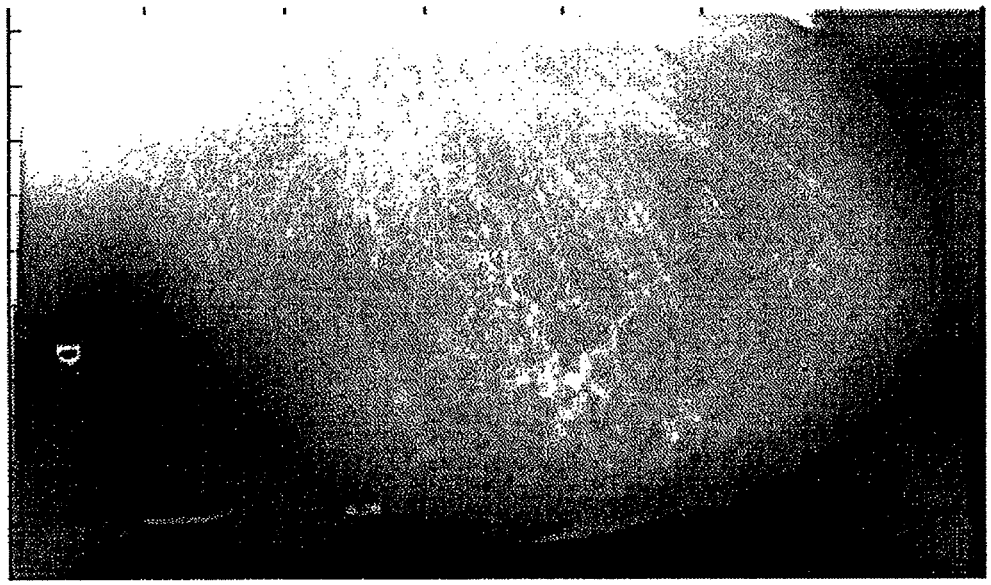
FIG. 11C Reconstruction of original mammogram from its phase and the averaged magnitude of FIG. 10A and FIG. 11A
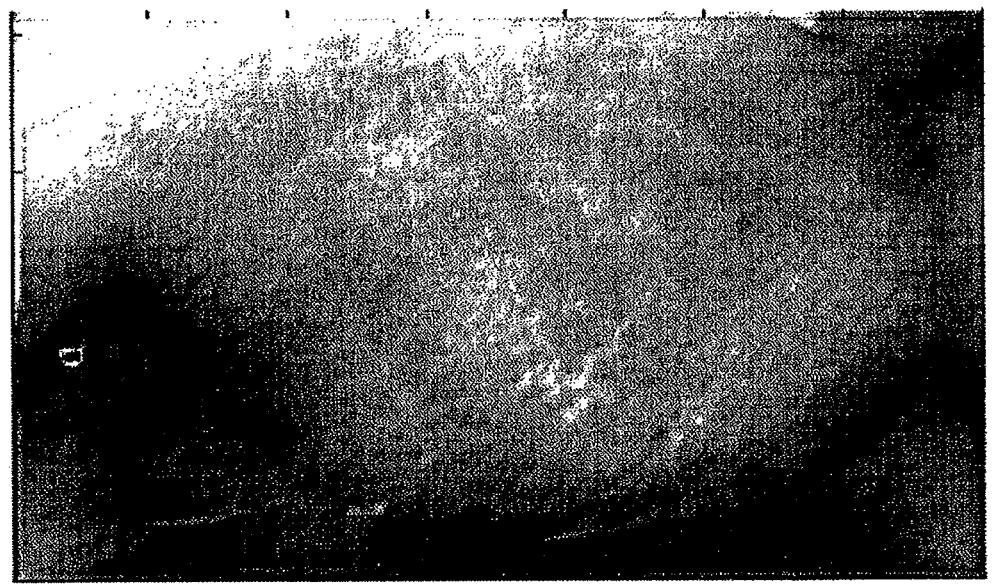
FIG. 11B Reconstruction of original mammogram from its phase and the magnitude of FIG. 10A

FIG. 11E  Contrast adjusted image of FIG 11D
FIG. 11D  Phase only image reconstruction of FIG 11A

FIG. 12B  Phase only image Reconstruction of FIG. 12A
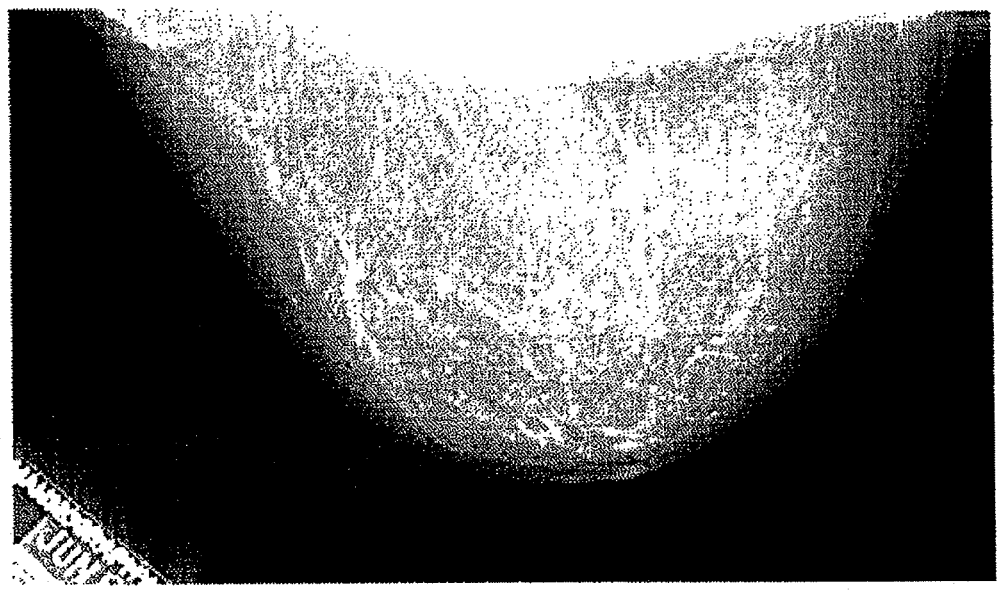
FIG. 12A  Original digital mammogram: LCC view

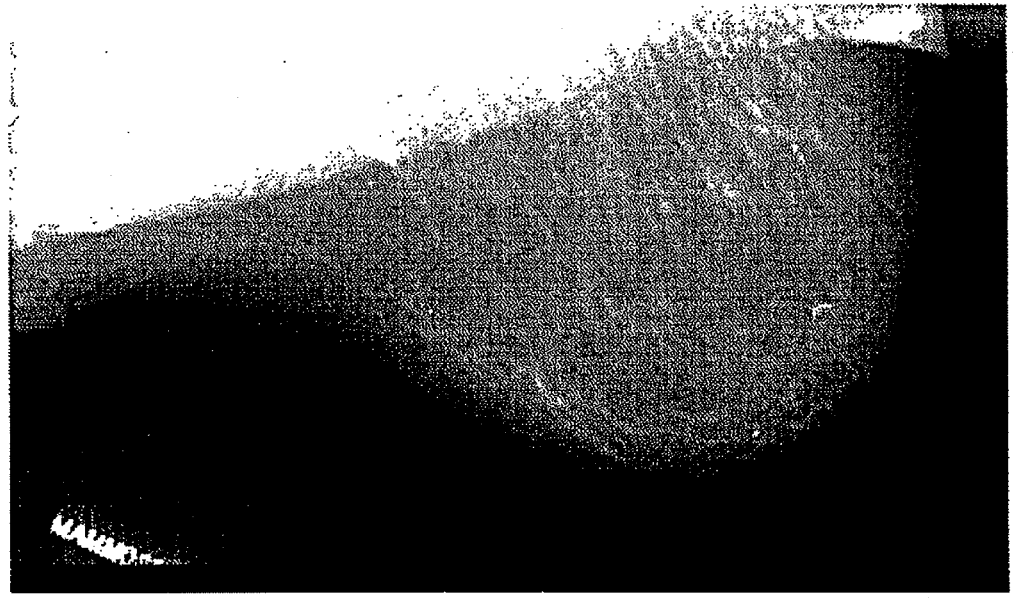
FIG. 13A  Original digital mammogram: LMLO view
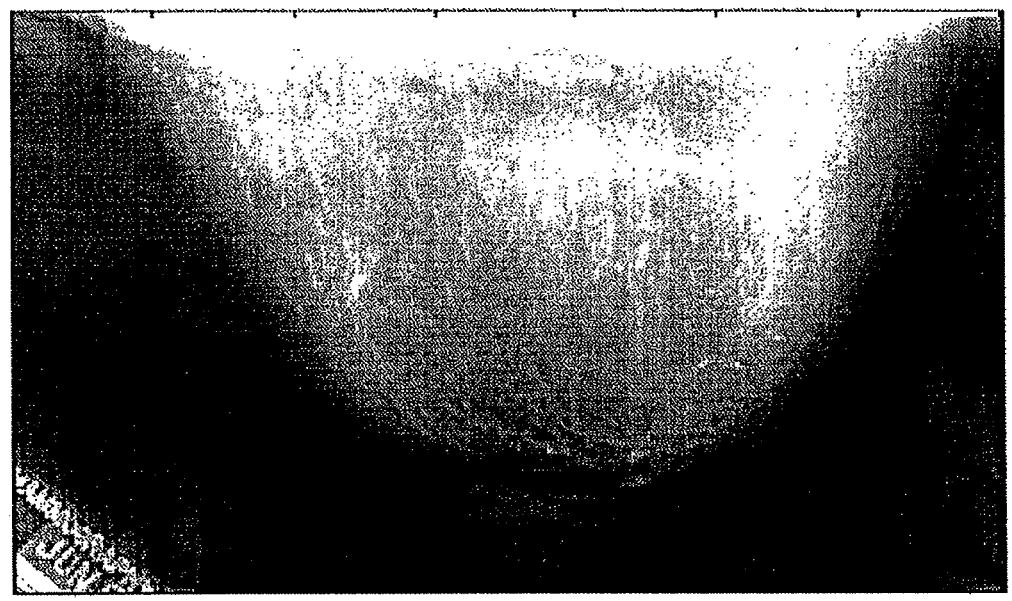
FIG. 12C  Reconstructed LCC

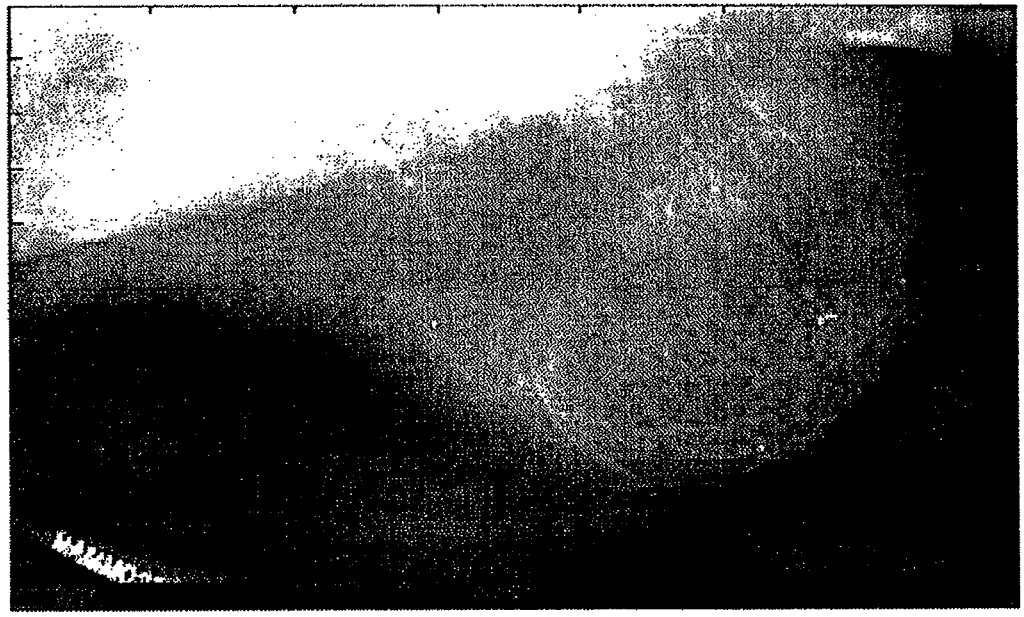
FIG. 13C  Reconstructed LMLO
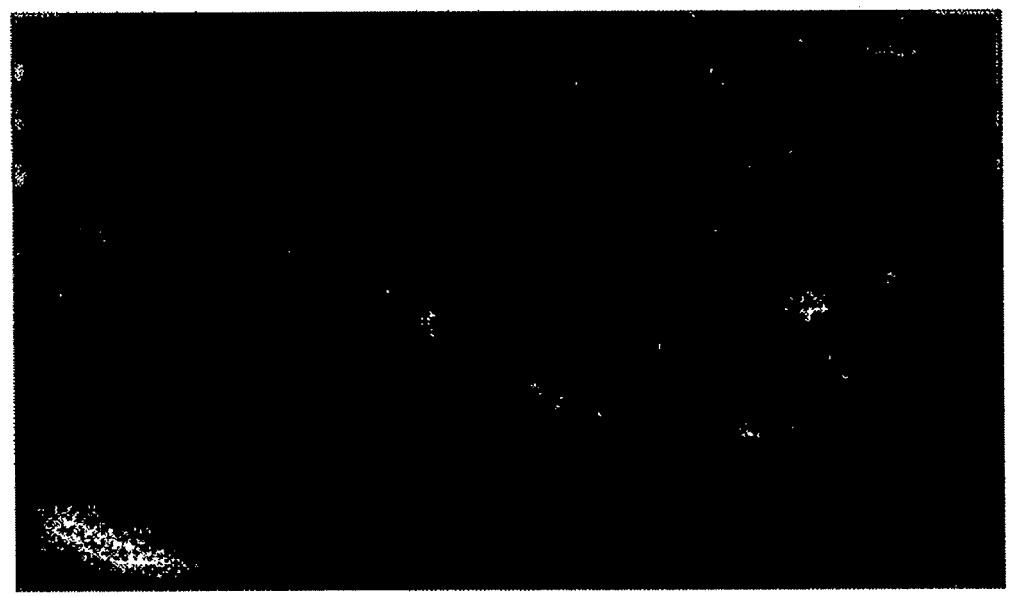
FIG. 13B  Phase only image Reconstruction of FIG. 13A

FIG. 14B  Phase only image Reconstruction of FIG. 14A
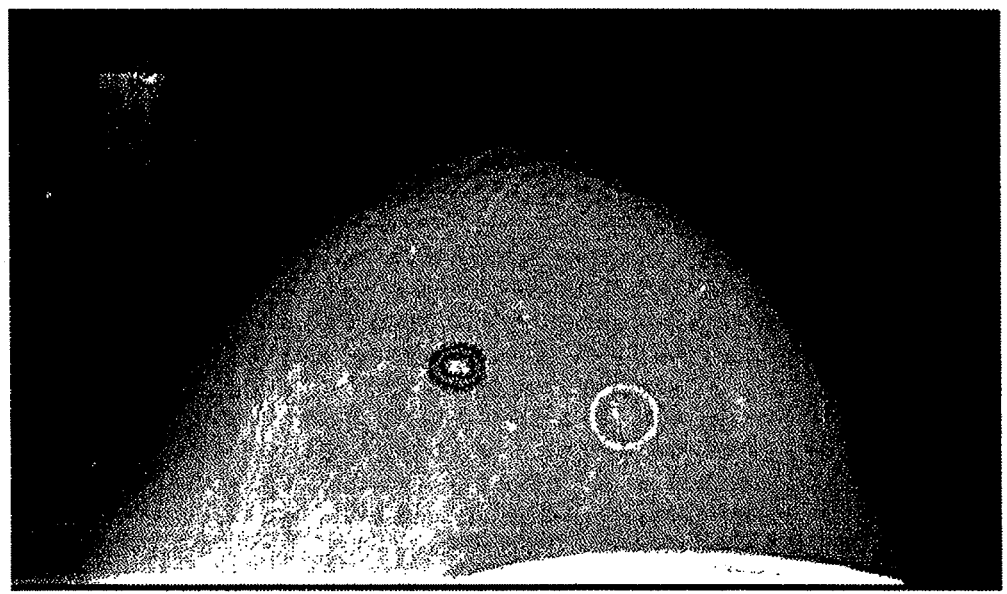
FIG. 14A  Original digital mammogram: RCC view

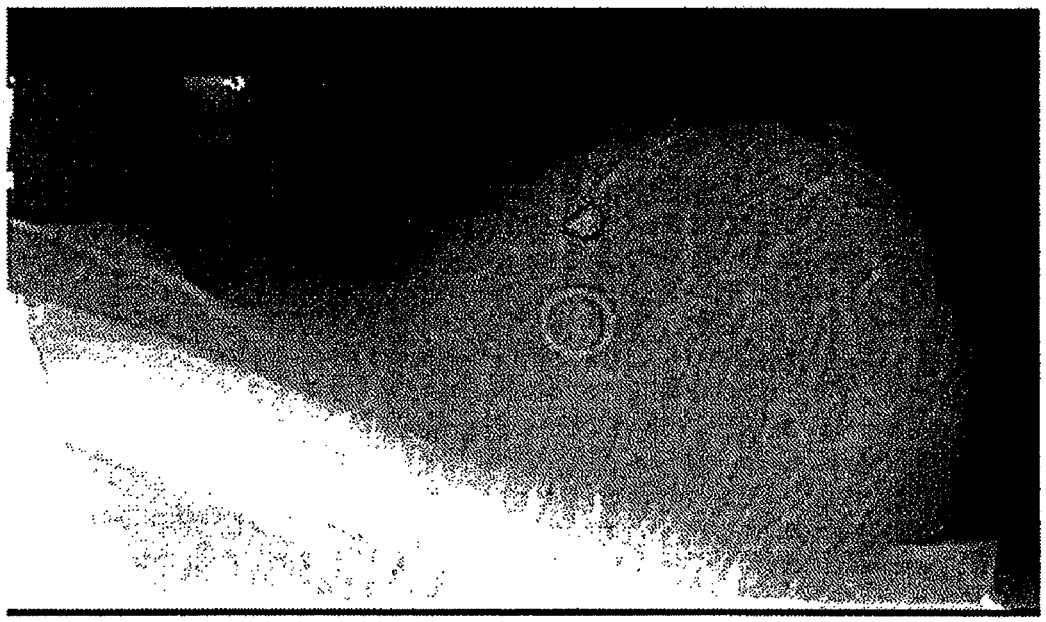
FIG. 15A Original digital mammogram: RMLO view
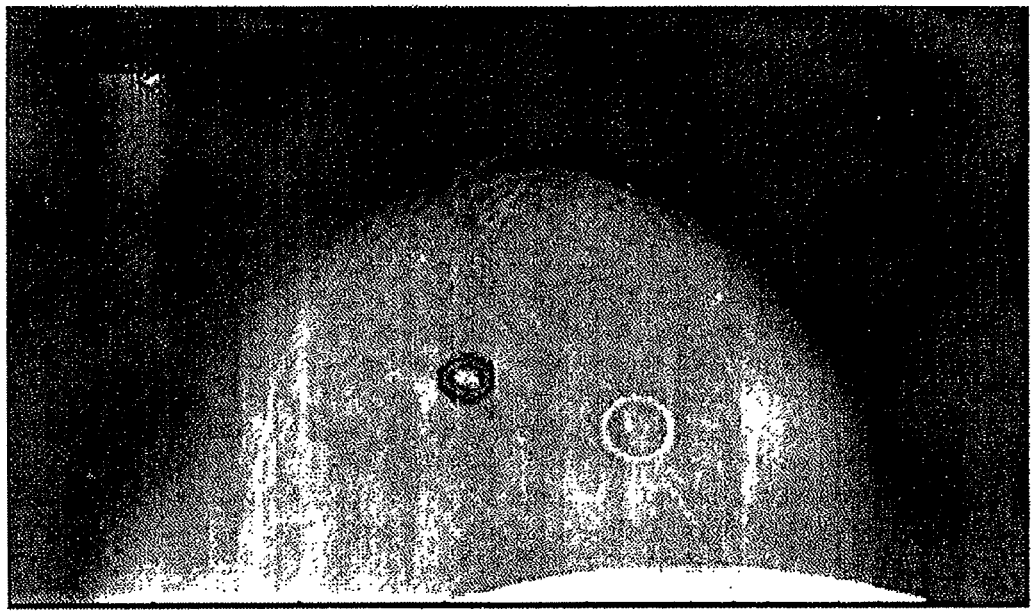
FIG. 14C Reconstructed RCC

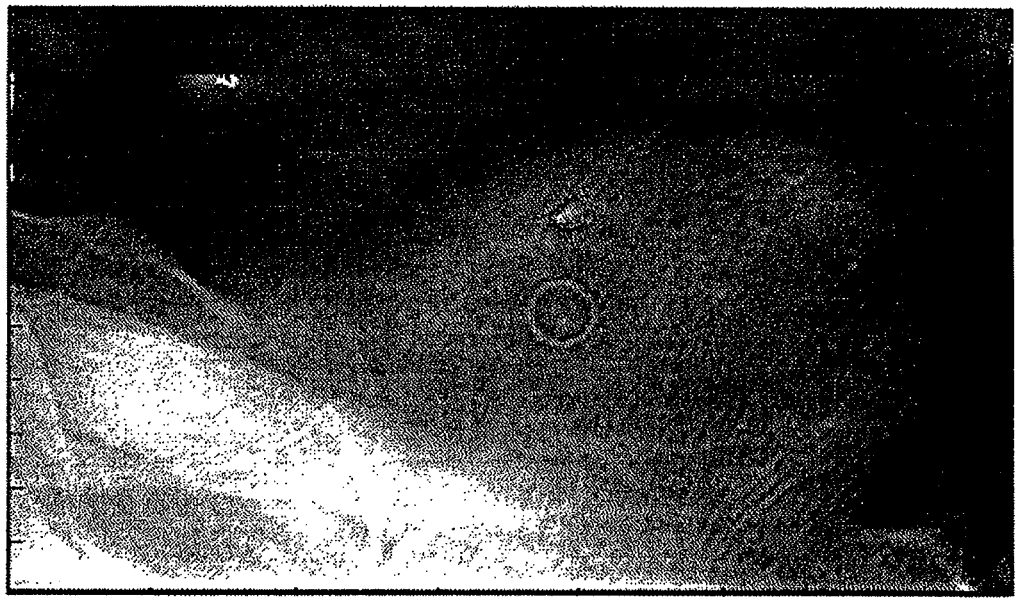
FIG. 15C Reconstructed RMLO
FIG. 15B Phase only image Reconstruction of FIG. 15A Mammogram I Original mammogram Mammogram I Reconstructed Image with magnitude of mammogram I and phase of FIG. 16A

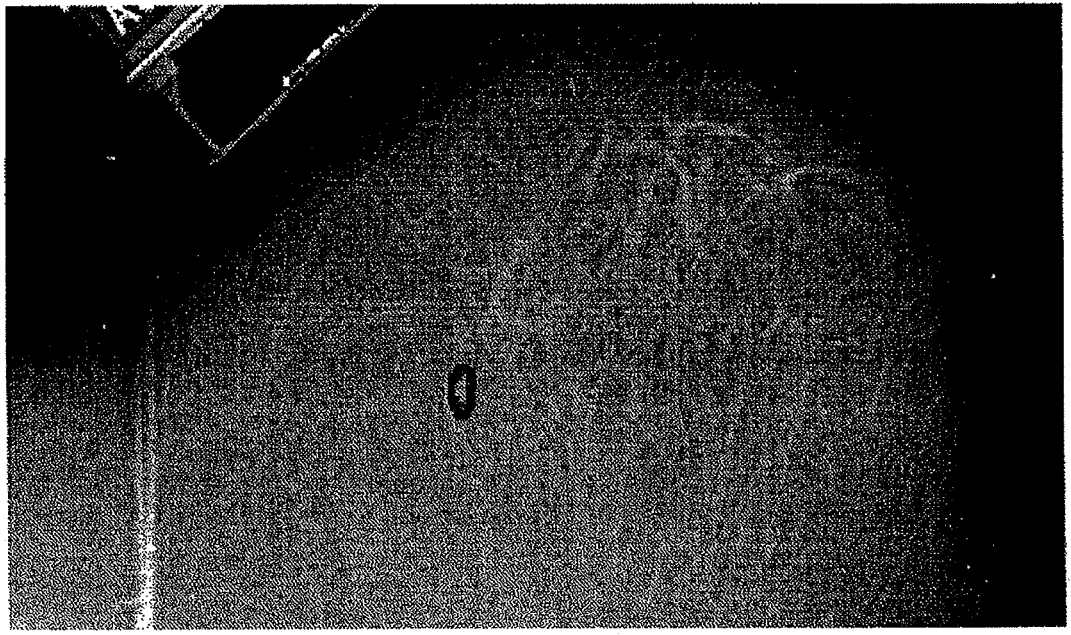
FIG. 16F Mammogram III
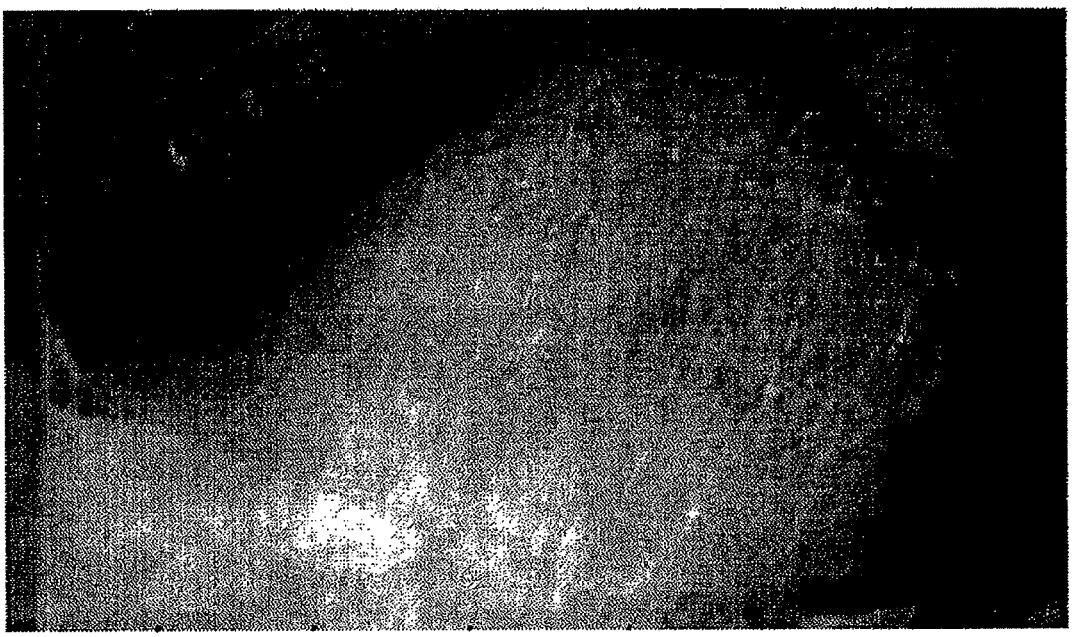
FIG. 16E Reconstructed Image with magnitude of mammogram II and phase of FIG. 16A Mammogram IV Reconstructed Image with magnitude of mammogram III and phase of FIG. 16A Reconstructed Image with magnitude of mammogram IV and phase of FIG. 16A

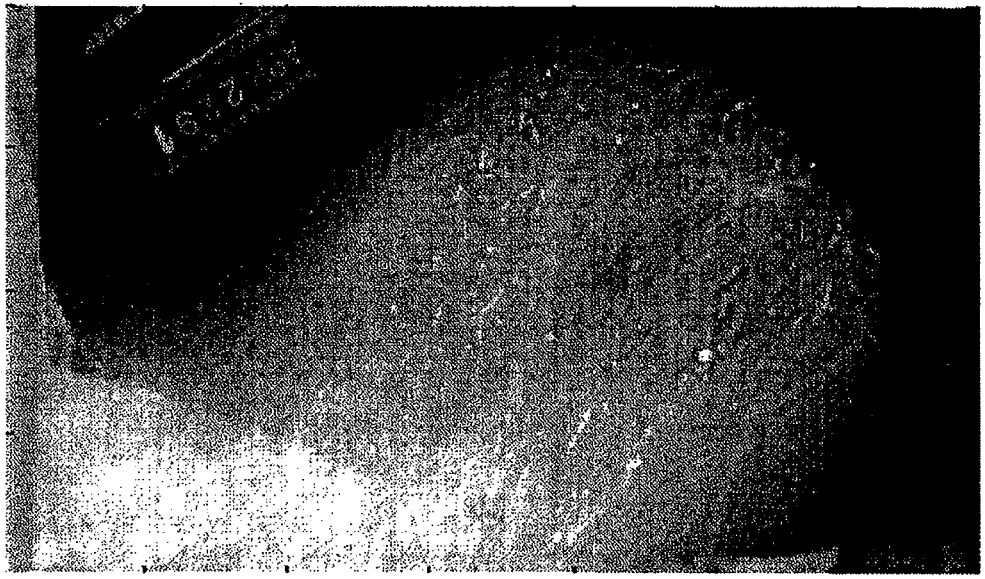
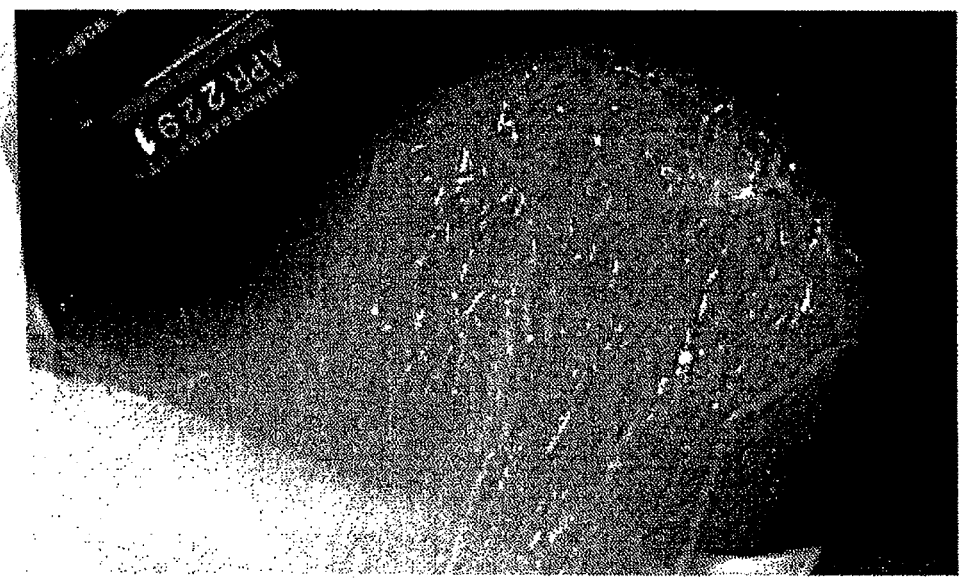
Original Mammogram and its reconstructed image with magnitude averaged over ensemble of mammogram I, mammogram II, mammogram III, mammogram IV and phase of original mammogram.
FIG. 16J An algorithm for phase only correlation of prior and current digital images.

Reference image f(x,y)

Auto correlation spot

Auto correlation peak value = 3.62'

Target image g(x,y)

Auto correlation spot

Discrimination Ratio
DCR = 1.827/3.627
50.3%

Cross correlation peak value = 1.827

Reference image f(x,y)

Target image g(x,y)

Discrimination Ratio
DCR = 1.9749/3.3614
16.68%

Cross correlation peak value = 0.5540

Process for spectral phase subtraction

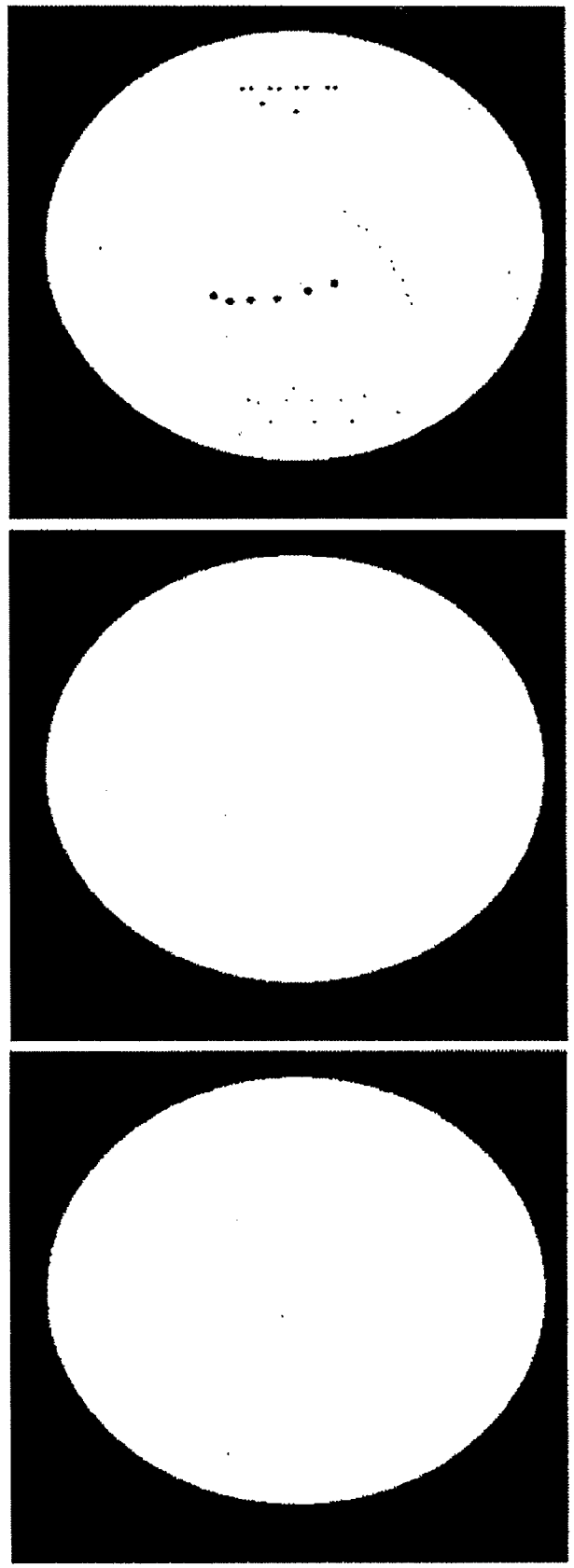
FIG. 27A Prior image p(x,y)
FIG. 27B Current image c1(x,y)
FIG. 27C Current image c2(x,y)

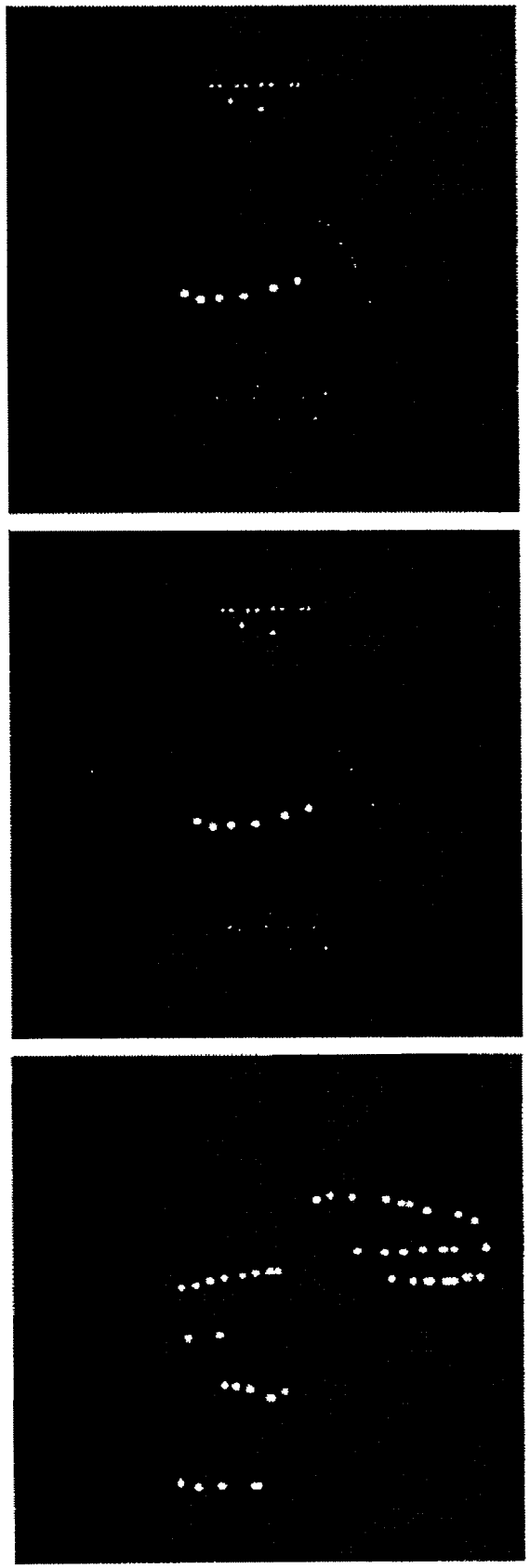

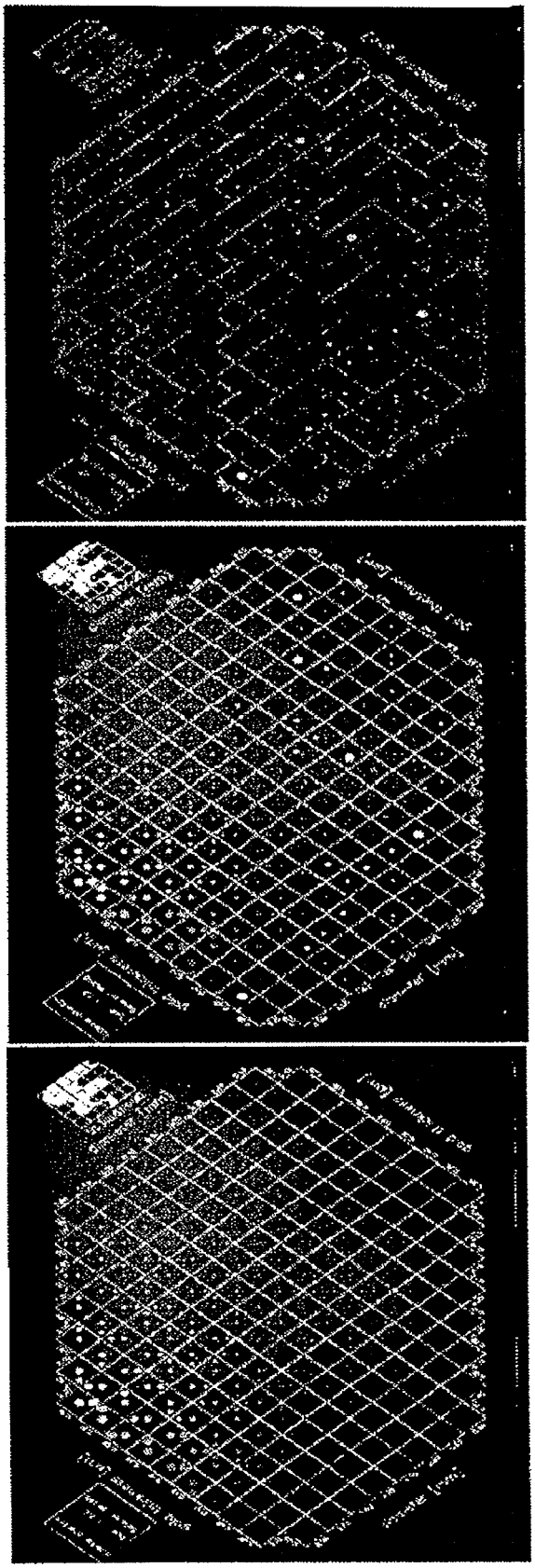
FIG. 29A shows the contrast detail (CD) phantom obtained used Full field digital mammography.
FIG. 29B shows some bright spots added to the image in A.
FIG. 29C displays the residual image reconstructed from spectral-phase subtraction using A and B.

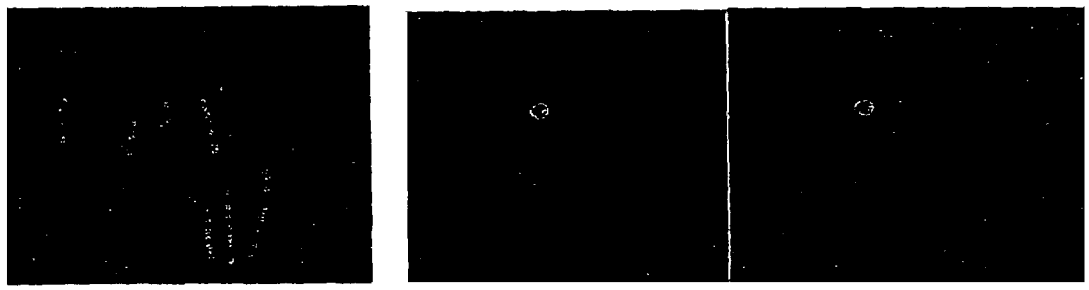
FIG30 Residual ph: (a) FIG 20-FIG21; (b) FIG20-FIG 22; (c) FIG21-FIG22

PHASE BASED DIGITAL IMAGING

CROSS REFERENCE TO RELATED APPLICATIONS

The present application claims priority to U.S. Provisional Patent Application No. 60/648,637 filed Jan. 28, 2005. The entire contents of the above application is incorporated herein by reference.

STATEMENT REGARDING FEDERALLY SPONSORED RESEARCH AND DEVELOPMENT

This invention was supported, in whole or in part, by grant 1R21CA89673-01A1 from The National Institutes for Health. The Government has certain rights in the invention.

BACKGROUND OF THE INVENTION

There are numerous features in the human body in which medical imaging techniques can be used effectively to assist in the diagnosis and treatment of medical conditions. Various diseases or conditions involve calcified materials, structures or deposits within the human body that are indicative of the medical condition of the patient. These can include features of the human skeleton, such as the spine, calcified deposits within the arterial system such as obstructions to blood flow in the coronary arteries, or microcrystalline deposits in breast tissue that can become cancerous. Breast cancer, for example, is one of the most frequently diagnosed malignancies and the second largest cause of cancer deaths in American females. Several improvements in diagnostic protocols have enhanced our ability for earlier detection of breast cancer, resulting in improvement of therapeutic outcome and an increased survival rate for breast cancer victims. Triple assessment is involved in identification of breast cancer. They are (1) clinical examination, (2) radiological assessment using mammography or ultrasound for example and, (3) pathological assessment using cytology or biopsy.

Although an impressive array of body-imaging techniques, such as x-ray imaging, x-ray computed tomography, magnetic resonance imaging, thermal infrared imaging (TIR), ultrasound, and radioisotope imaging are currently available to yield useful information, there are important limitations of safety, resolution, cost, and lack or limited specificity to key chemicals or structures necessary for functional body monitoring.

On the other hand, x-ray mammography, the current standard for monitoring breast cancer, has been shown to be effective in screening asymptomatic women to detect breast cancers. Abnormalities detected in mammography are classified as: Spiculated masses, Stellate lesions, Circumscribed masses, and microcalcification. Mammography is extremely useful in identifying pre-cancerous microcalcifications. Microcalcifications are found within the duct wall or lumen. Malignant microcalcifications are usually linear or branching whereas benign micro calcifications are rounded and punctuate.

This apparent positive benefit has resulted in a number of leading health care societies recommending that all women be screened using mammography on at least biennial basis. In order for mass screening to be cost effective, methods need to be developed to achieve it with high accuracy and speed. Moreover, as the microcalcifications are imbedded in dense soft tissue, the diagnosis of mammograms is subjective and solely depends on the interpretations of the radiologist of the mammogram. At times, even for qualified personnel, it is difficult to interpret screening mammograms in large numbers. So an appropriate use of imaging processing techniques to enhance the important features of mammograms improves the specificity and objectivity of clinical cancer diagnosis.

SUMMARY OF THE INVENTION

The present invention relates generally to the field of medical imaging in which digital images can be acquired and used in the diagnosis and/or treatment of medical conditions. A preferred embodiment of the invention uses image processing techniques to separate the phase information from the acquired digital image to provide an enhanced diagnostic image. A preferred embodiment of the invention is particularly useful for the identification and imaging of those features of the animal or human body which cause high spatial frequency features in the acquired image. Hard tissue structures such as bone or calcified or crystalline masses, lesions or cysts can cause such a high spatial frequency response making them suitable for phase component imaging.

Mammograms are now being acquired in digital format thereby allowing the use of digital image processing techniques such as the fast Fourier Transform, to enhance the identification of microcalcifications. A preferred embodiment of the present invention employs phase-only image reconstruction of digital mammogram that uses only high spatial frequency components, that show microcalcifications and contours of lesions and other masses of interest in a dark background. The phase-only information can be processed with averaged amplitude information to reconstruct the original digital image.

Preferred embodiment of the invention involve the phase imaging to provide images of obstructions within the arterial system, including the coronary arteries, to detection off kidney stones, of hairline fractures and other abnormalities within the skeletal system including the spinal column.

A preferred embodiment of the invention employs a digital imaging detector to acquire images from a region of interest. A patient support such as a table can be used to position a region of interest of the patient relative to an energy source such as an x-ray tube of a radiographic imaging system such as a computed tomography system or a mammography system. The imaging device provides image data to a data processor such as a computer having a memory, an image processor, a display and a user interface. A software program can be employed to provide phase-only image processing in accordance with the invention.

The foregoing and other features and advantages of the system and method for phase based digital imaging will be apparent from the following more particular description of preferred embodiments of the system and method as illustrated in the accompanying drawings in which like reference characters refer to the same parts throughout the different views.

BRIEF DESCRIPTION OF THE DRAWINGS

FIGS. 4A and 4B show a contrast detail digital image of a phantom with embedded gold particles obtained using a full field digital mammography system and a phase-only image, respectively.

FIGS. 5A, 5B and 5C are an original mammogram, a phase-only image and a contrast adjusted phase-only image, respectively.

FIGS. 6A, 6B and 6C are an original mammogram, a phase-only image and a contrast adjusted phase-only image, respectively.

FIGS. 7A, 7B and 7C are an original mammogram, a phase-only image and a contrast adjusted phase-only image, respectively.

FIGS. 8A, 8B and 8C are an original mammogram, a phase-only image and a contrast adjusted phase-only image, respectively.

FIG. 9 illustrates a process sequence in accordance with a preferred embodiment of the invention.

FIGS. 10A-10E show and original mammogram and processed images in accordance with the invention.

FIGS. 11A-11E show an original mammogram and processed images in accordance with the invention.

FIGS. 12A-12C show an original mammogram and processed images in accordance with the invention.

FIGS. 13A-13C show an original mammogram and processed images in accordance with the invention.

FIGS. 14A-14C show an original mammogram and processed images in accordance with the invention.

FIGS. 15A-15C show an original mammogram and processed images in accordance with the invention.

FIGS. 16A-16J show an original mammogram and processed images in accordance with the invention.

FIGS. 27A-27C show original images for spectral phase subtraction.

FIGS. 28A-28C show processed images from FIGS. 27A-27C.

FIGS. 29A-29C show contrast detail of phantom and processed images.

FIGS. 30A-30C show residual images based on FIGS. 20-22.

DETAILED DESCRIPTION OF THE INVENTION

A preferred embodiment of the present invention is the phase characteristics of Fourier transform of medical images for computer aided diagnosis (CAD). We propose phase-only image reconstruction, original image reconstruction from phase-only information, phase-only correlations, spectral phase subtraction techniques for comprehensive CAD.

Figure 1A:
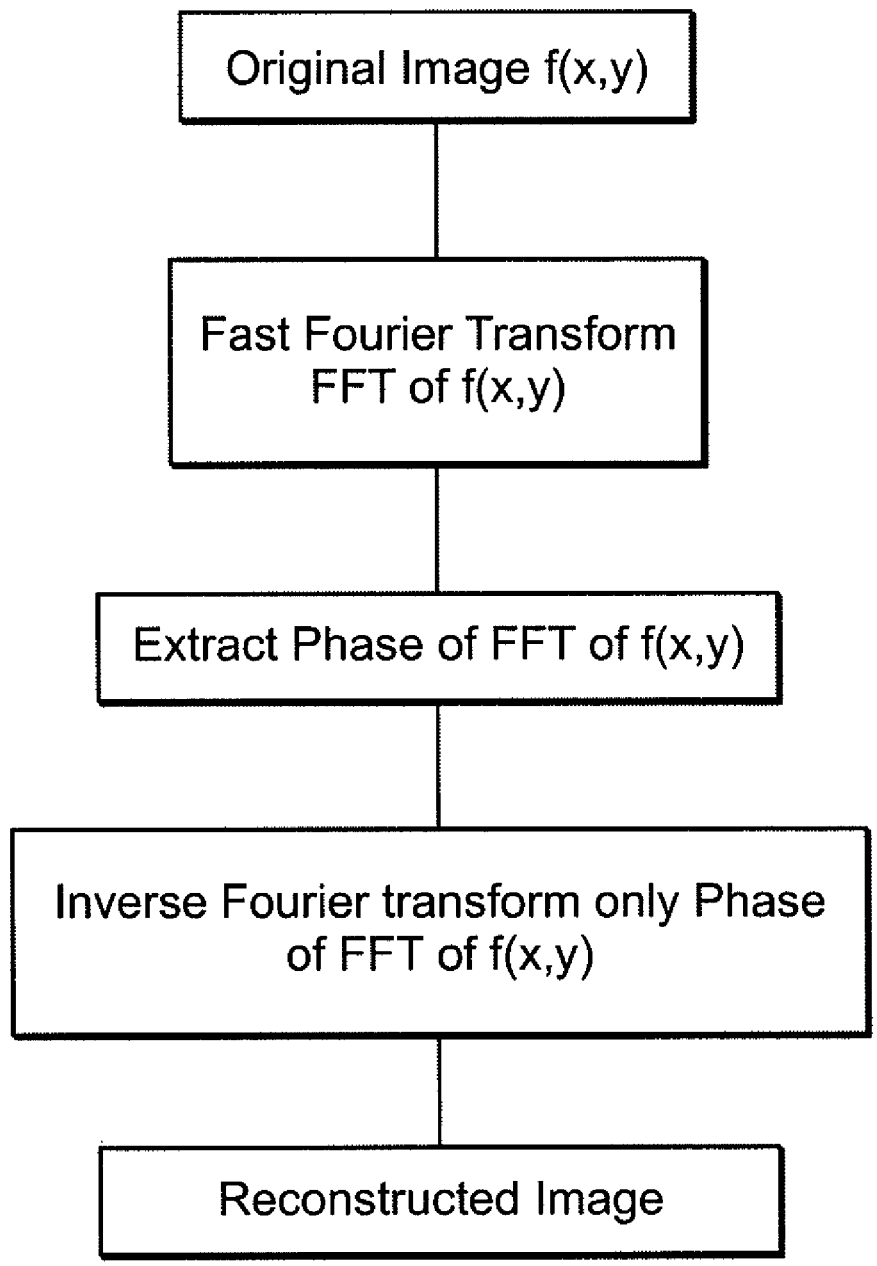
FIG. 1A illustrates a method of forming an image of a region of interest of a patient in accordance with the preferred embodiment of the invention.

The method for phase-only image reconstruction is shown in FIG. 1A. Original digital image (digital mammogram, digital chest x-ray or in general any digital radiograph) is Fast Fourier Transformed using a programmed FFT sequence stored on a computer. The phase angle of the FFT spectrum is calculated. The phase of low spatial frequencies in the Fourier spectrum is zero or close to zero, while the phase of high spatial frequencies is in the neighborhood of $\pm\pi$. From this phase angle, a phase-only function with unit amplitude transmittance is generated. The phase-only function is inverse Fourier transformed using another FFT operation to obtain a phase-only image. This phase-only image predominantly contains high spatial frequency components.

Microcalcifications are tiny regions of calcium in the breast. In digital mammograms these microcalcifications appear in small clusters of a few pixels with relatively high intensity compared with their neighboring pixels that belong to soft dense tissues in the breast. Given that the microcalcifications belong to high spatial frequency components of the Fourier spectrum of a digital mammogram, detection of microcalcifications is achieved by reconstructing the phase-only image. The low spatial frequency components (corresponding to the soft dense tissue) have zero phases and are suppressed in the phase-only image. Another important change seen on the mammogram is the presence of mass, which may occur with or without associated calcifications. A mass is any group of cells clustered together more densely than the surrounding tissue. The size, shape and margins (edges) of the mass help the radiologist in evaluating the likelihood of cancer. Since a mass differs in its gray-value with respect to the surrounding tissue in the mammogram, edges of the mass correspond to high spatial frequencies. The phase-only information of a mammogram with such masses shows the shape and edges of the mass.

Figure 1B:
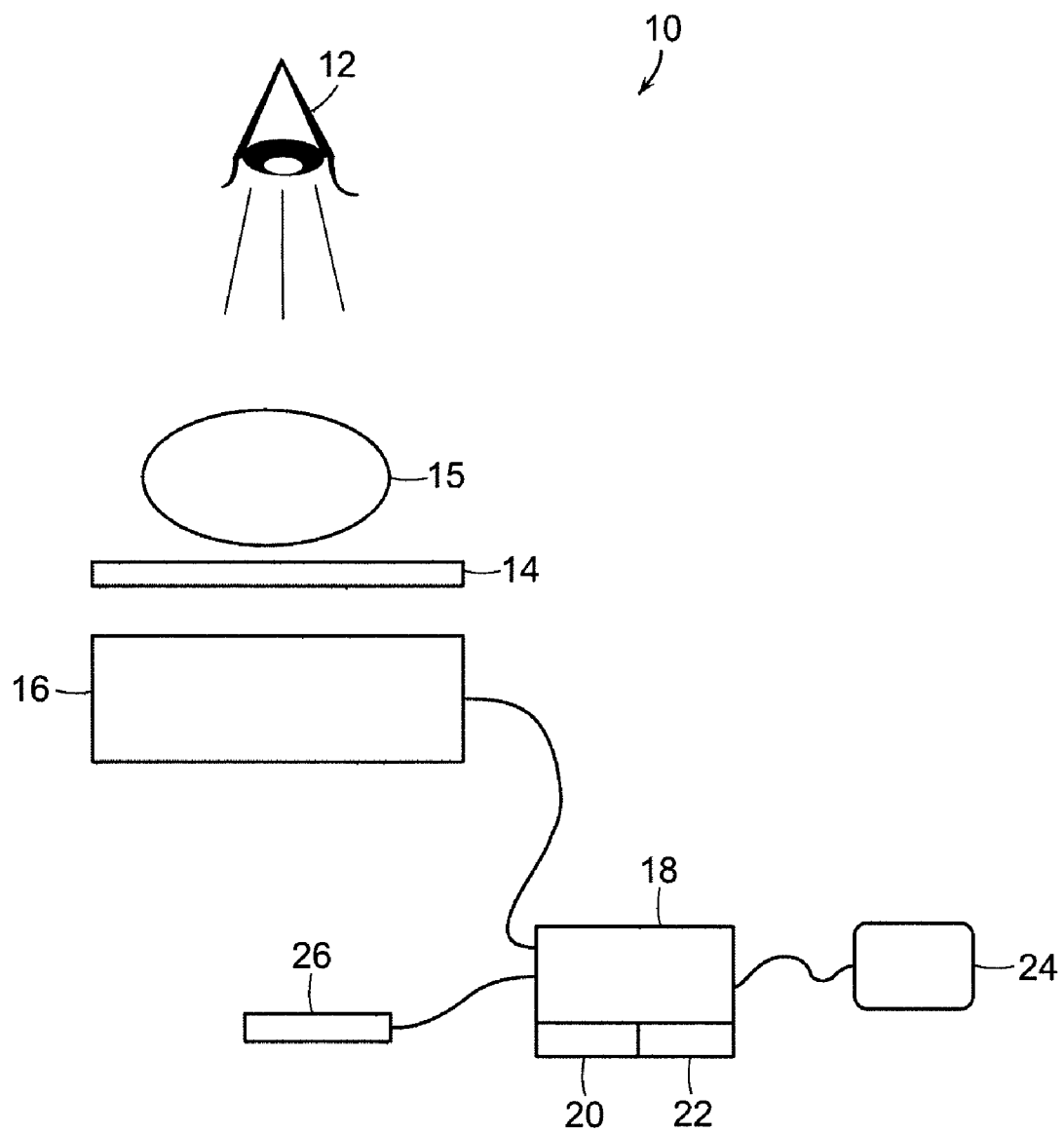
FIG. 1B illustrates a digital radiographic acquisition system in accordance with the present invention.
Figure 2B:
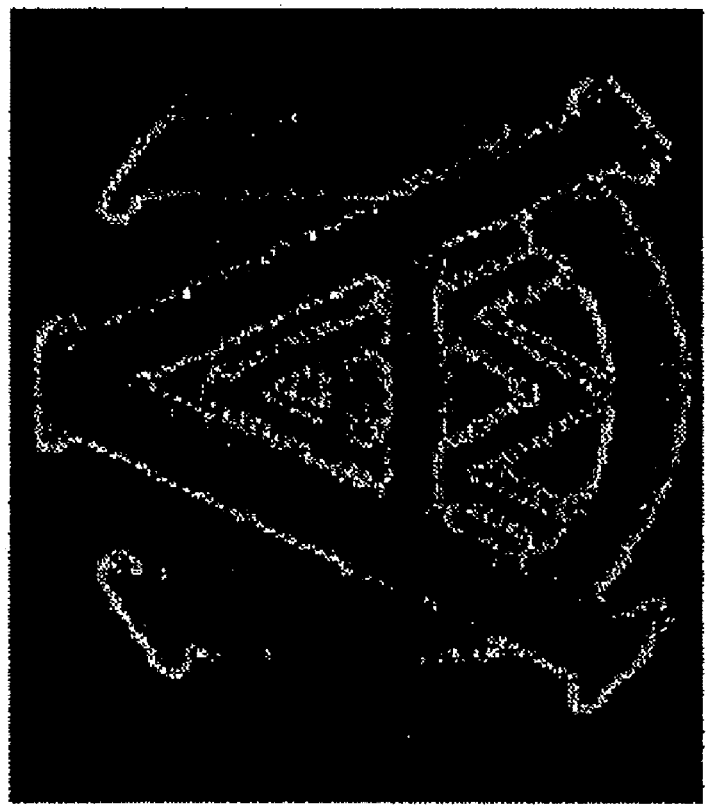
FIGS. 2A and 2B show an original image and a phase-only image with edge enhancement, respectively.
Figure 2A:
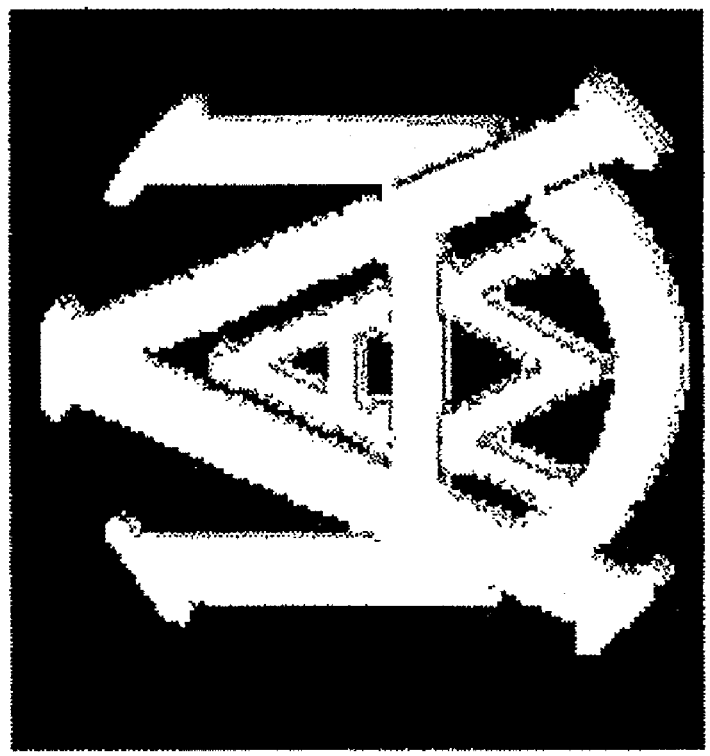

Digital radiographs can be acquired using a system 10 such as that illustrated in FIG. 1B. This includes an x-ray source 12, a table 14 on which a patient 15 lies, a detector system 16 for detecting x-ray radiation that is transmitted through the patient. The detector system is connected to a computer 18 having a memory 20 and an image processor 22, a display 24 and a user interface 26 such as a keyboard. The computer 18 can be connected to a public access network such as the Internet, a local area network, or connected remotely to a remote network, server, computer workstation, or other databases. The detector system includes a digital detector such as a charge coupled device, a CMOS imaging detector, an amorphous silicon detector or other digital image detector employing a scintillator, or alternatively, it can be a detector that converts x-rays into electrical signals.

Figure 3B:
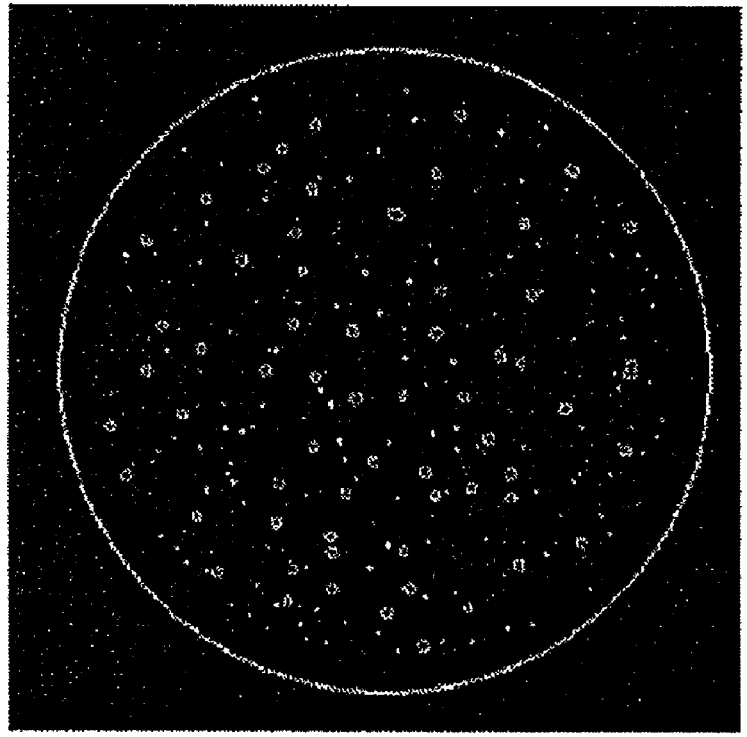
FIG. 3 shows a phase-only image of a phantom with simulated microcalcification.
Figure 3A:
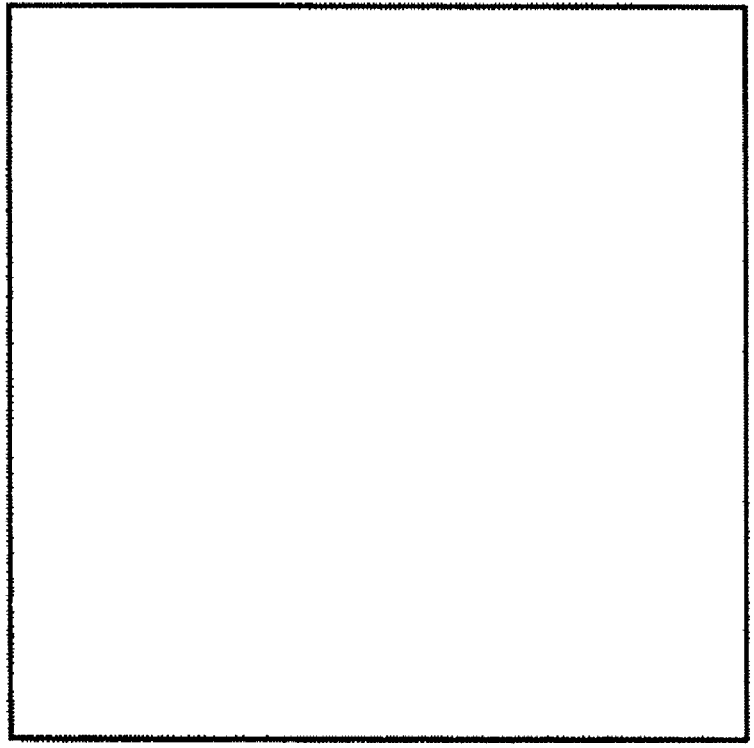
Figure 4A:
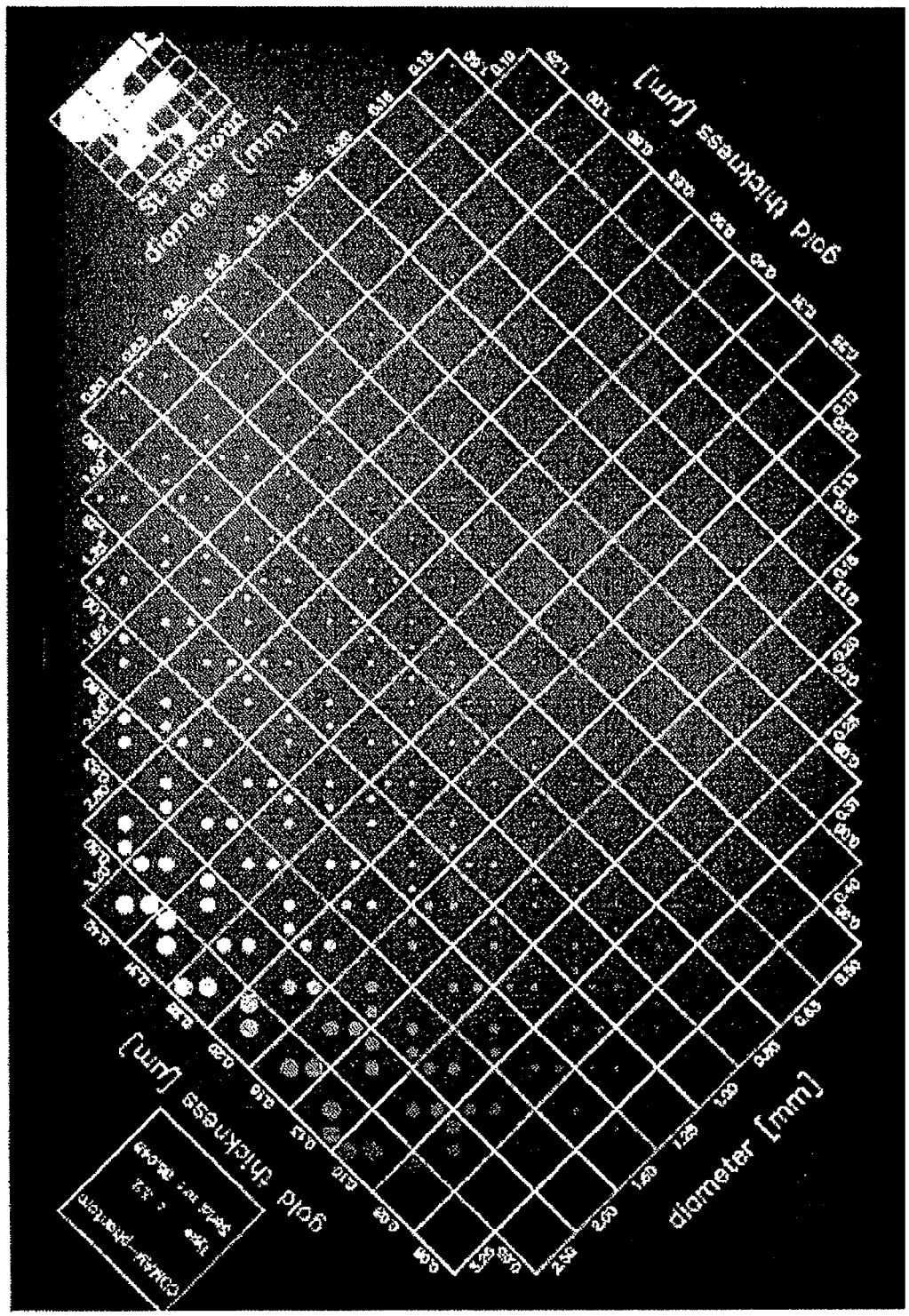
Figure 8C:

FIGS. 2A-2B, FIG. 3 and FIGS. 4A-4B show results of phase-only image reconstruction of digital phantoms. A digital phantom with invisible simulated microcalcifications which differ in brightness with respect to surrounding pixels are not visible while FIG. 3 shows a phase-only image reconstructed with only microcalcifications having good contrast. FIG. 4A is Contrast digital phantom with embedded tiny gold particles obtained from Full Field Digital mammography machine. FIG. 4B is the phase-only image of FIG. 4A. It clearly shows embedded small gold particles as tiny bright spots while little bigger size gold particles are shown with their shape and edges. FIG. 5A, FIG. 6A, FIG. 7A, and FIG. 8A show clinical digital mammograms and FIG. 5B, FIG. 6B, FIG. 7B, and FIG. 8B show the corresponding phase-only images. The microcalcifications are shown as bright spots in the dark background providing a many-fold increase in the contrast compared to the original image.

The advantage of this technique in detection of microcalcifications over conventional digital image processing techniques is, it doesn't depend on the density of soft tissue in the breast that appear as a background (DC components) in the mammogram. In other words the technique is self adaptive to the changes in the background as the phase of low spatial frequency is zero. On the other hand other image processing techniques that involve high pass and band pass filters, the filter size and threshold have to be adjusted depending on the type of background in the mammogram. The system of the present invention provides a phase only that image preserves the morphology and texture.

The phase-only image reconstruction can in general be applies to any digital radiographic image, digitized radiographic image, and Magnetic Resonance images (MRI) and Computed Tomography (CT) such as coronary calcifications in Cardiac CT images to extract and view essential features of the image hidden in the background of the image.

A method of reconstructing an original digital mammogram from its phase-only information is shown in FIG. 9. It is common practice in mammography to obtain 4 different views of breast x-ray images, namely LCC, LMLO, RCC and RMLO. All of the images are Fourier transformed using an FFT sequence. The phase angle and spectual-magnitude of the Fourier spectrum for each image are extracted. The average magnitude is obtained by averaging the spectual magnitude over an ensemble of these images. The extracted phase-only information of each image is multiplied to this average magnitude. The resulting product of each image is then inverse Fourier transformed using the programmed FFT sequence to reconstruct the original image. These reconstructed original images preserve all the essential features of the respective original images including the morphology and texture.

Figure 10B:
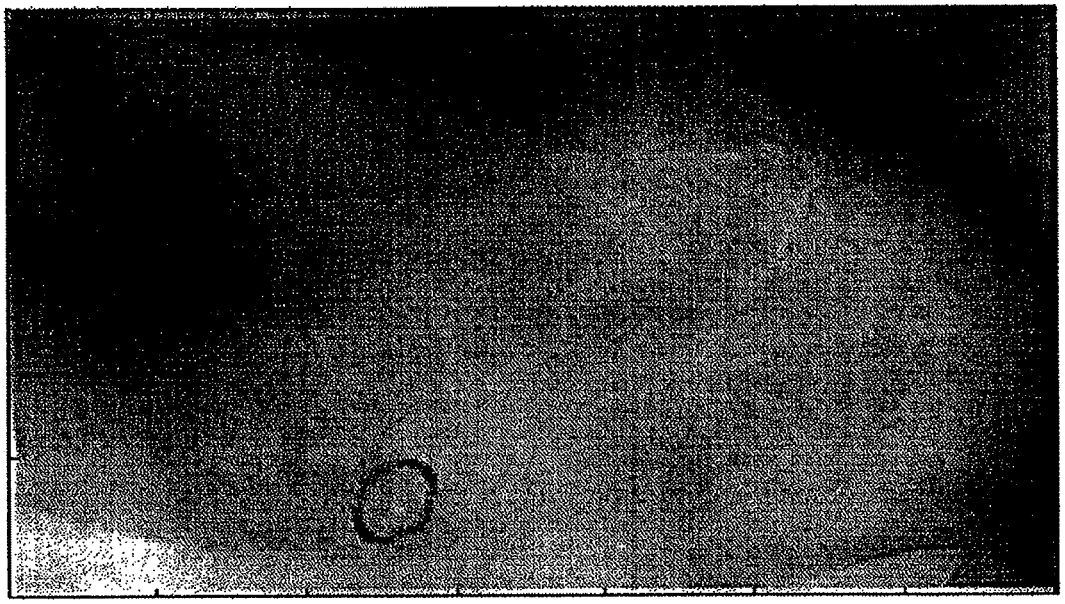
Figure 10A:
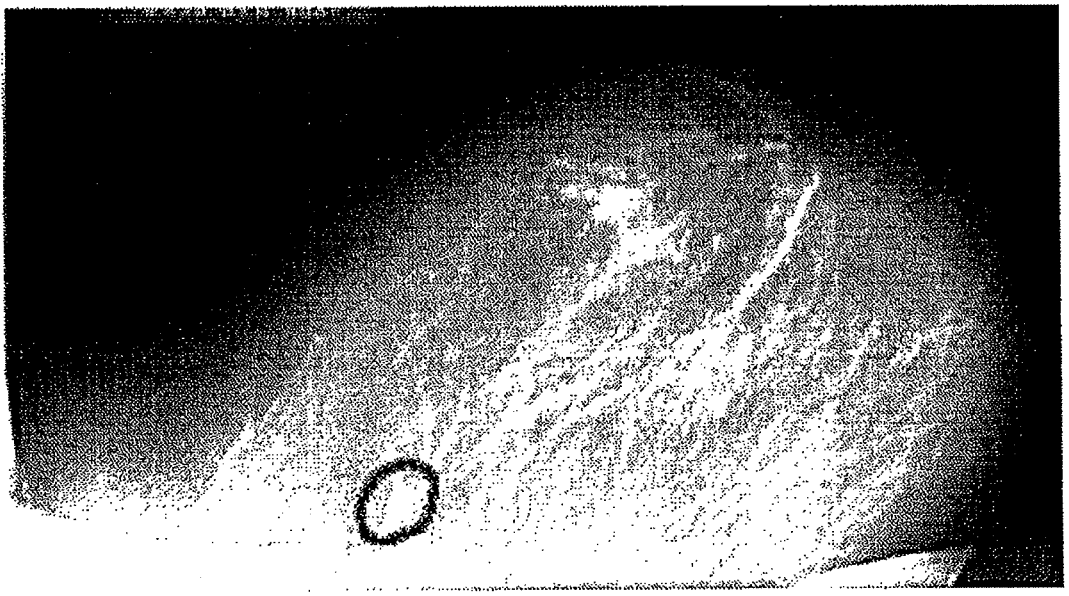
Figure 10D:
Figure 10C:
Figure 16B:
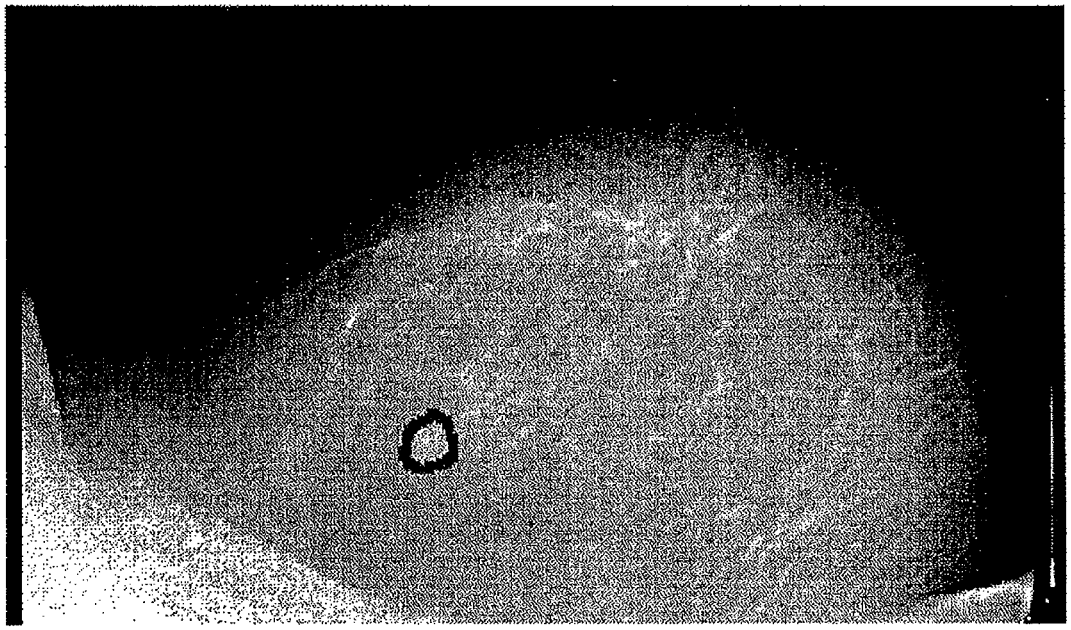
Figure 16A:
Figure 16D:
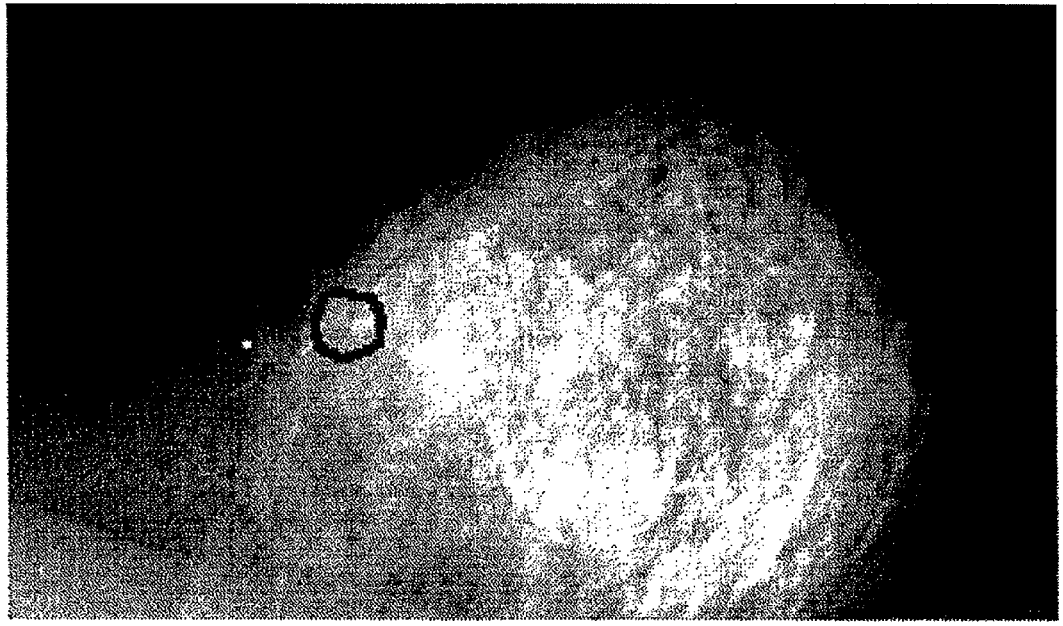
Figure 16C:
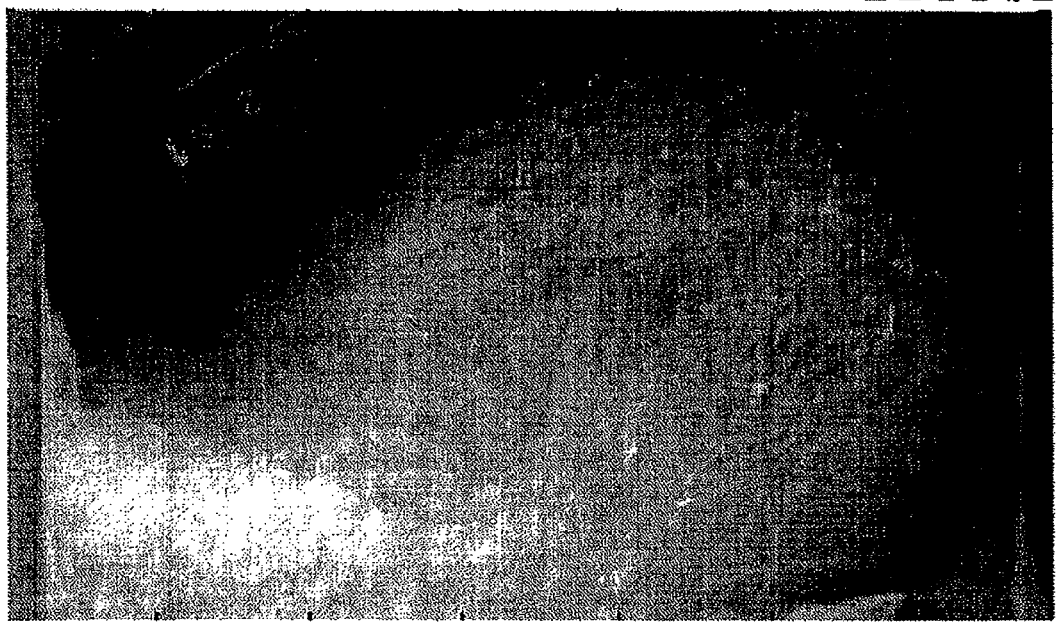
Figure 16H:
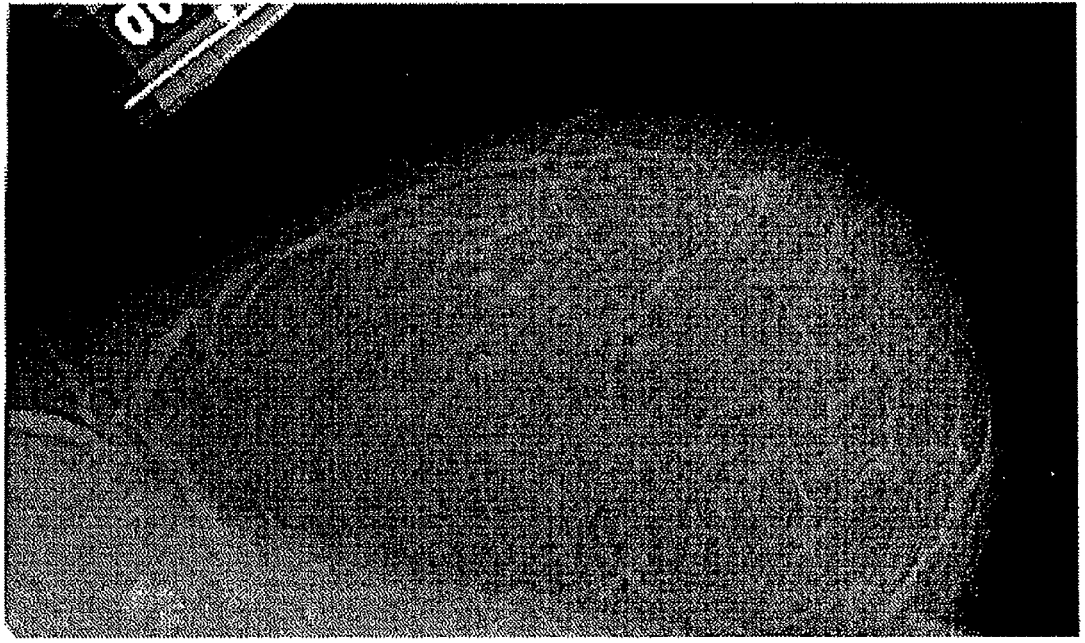
Figure 16G:
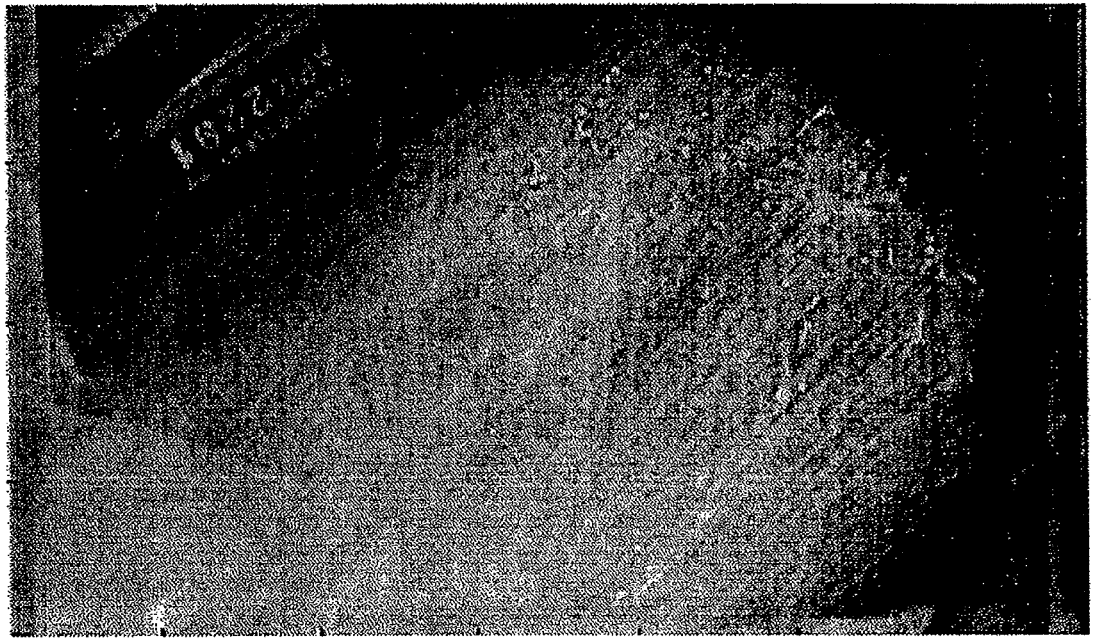
Figure 16I:
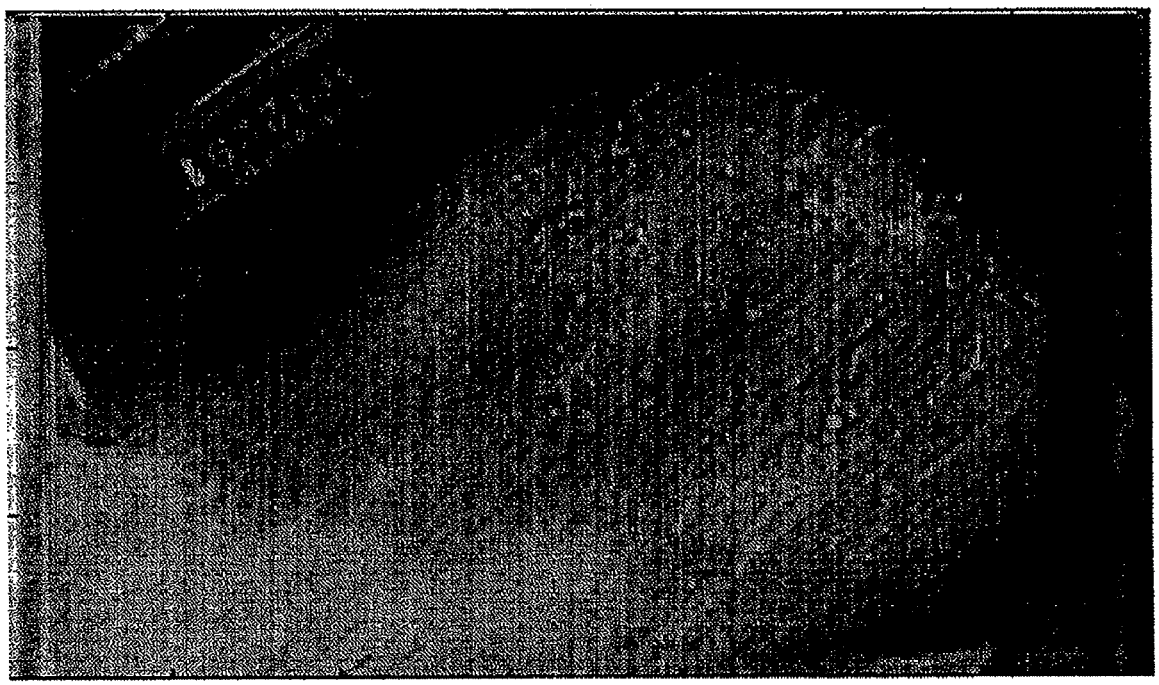

FIG. 10A and FIG. 11A are original digital mammograms of the same patient but of different views; RMLO and LMLO respectively. FIG. 10B and FIG. 11B show the original image reconstructed from its phase-only information but with magnitude of FIGS. 11A and 10A degradation. It is important to note that the phase-only information is essential in reconstructing the original image as it preserves all the significant features of the image and not the spectral magnitude. FIG. 10C and FIG. 11C show the reconstructed original images of FIGS. 10A and 11A reconstructed from their respective phase-only information but with representative magnitude averaged over individual spectral magnitudes of FIGS. 10A and 11A. It is evident from these figures that FIGS. 10C and 11C resemble more closely to the original image than FIG. 10B and FIG. 11B. Thus the magnitude averaged over the large ensemble of similar images gives a nearly original image reconstruction. The sequence shown in FIG. 9 uses digital mammograms of LCC, LMLO, RMLO and RCC views of a patient to generate the average magnitude. FIG. 12A, FIG. 13A, FIG. 14A and FIG. 15A show the LCC, LMLO, RCC, RMLO views of the patient while FIG. 12C, FIG. 13C, FIG. 14C, and FIG. 15C show corresponding reconstructed original images from the average magnitude. FIG. 12B, FIG. 13B, FIG. 14B, and FIG. 15B show corresponding phase-only images.

Radiologists are often under tremendous pressure while giving decisions based on mammogram readings. The tiny microcalcifications hidden in the background of dense soft tissue are clearly visible in some mammograms, barely visible in some and not visible at all in some. This is mostly due to density of soft tissue in the breast which varies from person to person and with age. For example younger women have denser breast tissues providing a bright background in the mammogram. It can be very difficult to interpret mammograms in these cases. It would be helpful to the radiologist if a training tool is available which can be used to extract information about microcalcifications and other masses from a known mammogram case, add this information to different backgrounds provided by the other mammograms from the same or other patients and see whether the added information can be detected.

The preferred method of reconstructing an image using its phase-only information and spectral magnitudes of images is useful for training the radiologist in his decision making process. For example, the subtle microcalcifications and other important features such as cysts and masses can be extracted from a mammogram using phase only image reconstruction. Using the process sequence shown in FIG. 9 this phase only information can be multiplied with the magnitude extracted from any other mammogram and used to determine whether they are able to detect the features being added. The results are shown in FIG. 16.

In clinical diagnosis, as well as in radiotherapy planning and evaluation, several images of one patient obtained using different imaging modalities or at different times, need to be compared. Although visual comparisons of available radiographic image with subsequent radiographic images are still standard practice as part of routine clinical evaluation, computerized analysis of these images has recently attracted the interest of both medical physicists and physicians alike. In this invention phase-only correlation and spectral phase subtraction techniques are used for tracking the development of useful information in digital radiographic images with respect to a selected time period.

Phase only correlation (POC) methods use the phase information of a reference image that is correlated with the phase information of an acquired image. Due to the absence of low spatial frequency components in the phase-only information the POC method produces a sharp correlation peak. The POC method is consequently preferred to the amplitude-only correlation and complex Fourier spectrum correlation techniques. This sharp correlation peak feature of POC technique is used for measuring translational, rotational and scale shifts in the medical images.

Phase-only information obtained from the phase of the Fourier transform suppresses the background due to soft dense breast tissue (low spatial frequency components) and predominantly contains information about essential features such a microcalcifications, shape and edges of masses and cysts (high spatial frequency components) in mammograms. The POC method can be used to correlate the phase-only information of a prior mammogram with phase-only information of a current mammogram.

Figure 17:
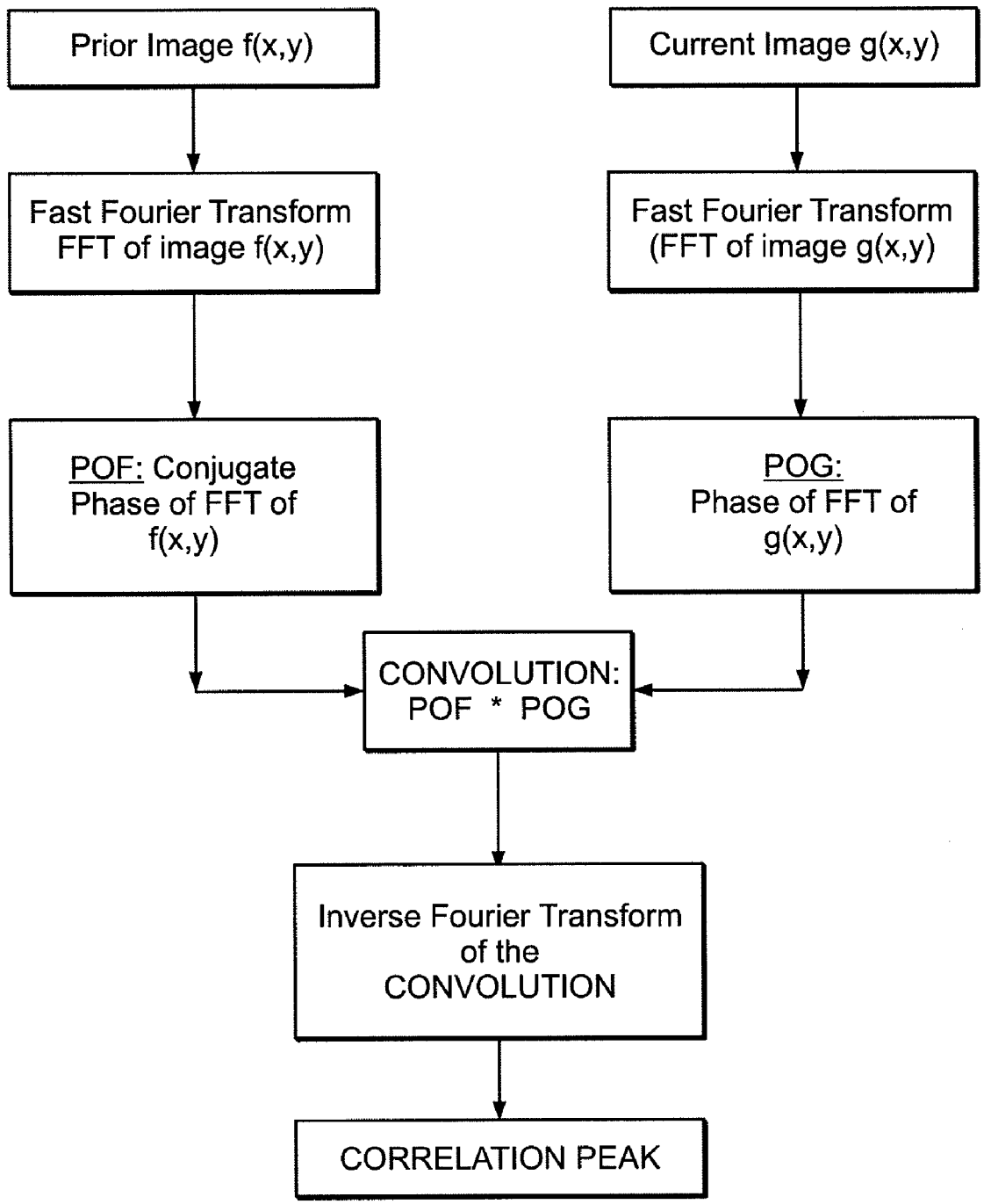
FIG. 17 illustrates a process sequence in accordance with the preferred embodiment of the invention.
Figure 18A:
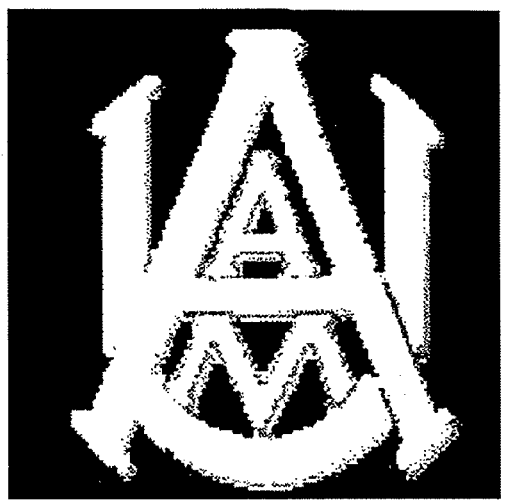
FIGS. 18A-18C show a reference image, auto correlation spot and peak value, respectively.
Figure 18B:
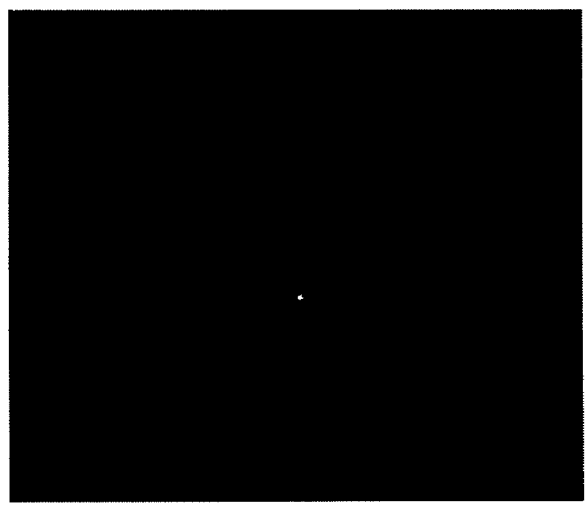
Figure 18C:
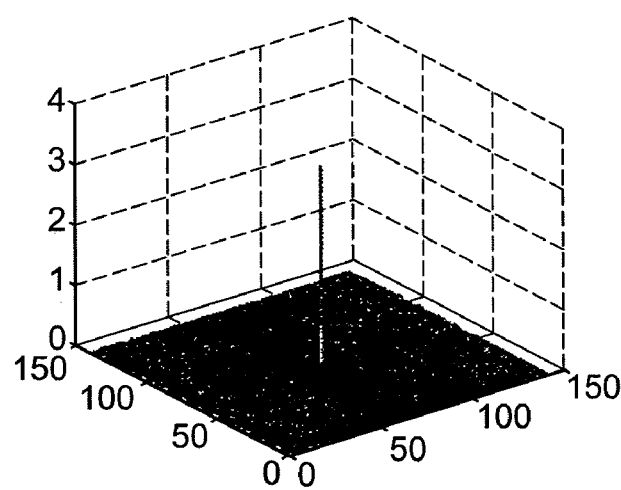
Figure 19A:
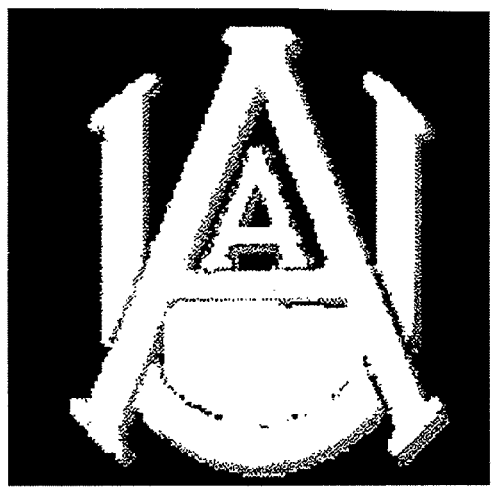
FIGS. 19A-19C show an image, auto correlating spot and cross correlation peak value, respectively.

The POC method shown in FIG. 17 can be used to calculate the discriminate ratio (percentage change in the said essential features of interest) between an image and its subsequent image (current) obtained at different time interval. Usually this time interval between the prior and the current image can be one month to a year depending on the seriousness of the case. When the image in FIG. 18A is used both as a reference and a target image in the sequence shown in FIG. 17, the output correlation peak is called auto correlation peak as shown in FIG. 18C with the peak value=3.627. When the image in FIG. 18A is slightly distorted as shown in FIG. 19A and used as a target image in the process sequence, the maximum correlation peak value, called cross correlation peak, drops to 1.827 (FIG. 19C). The ratio of maximum of cross correlation peak value to the auto correlation peak, drops to 1.827. The ratio of maximum of cross correlation peak value to the auto correlation peak value is called discrimination ratio (DR). For this example the DR is 50.37%, and indicated the percent change in the high spatial frequency components of the target image with respect to the reference image.

For example, when the patient is normal, there may not be any clusters of microcalcifications present in the breast and the corresponding mammogram (say MAMO1) will not show any sign of microcalcifications. When the patient obtains her next mammogram (say MAMO2) after a year of two, and she developed some microcalcifications in the breast, which are a sign of a cancer at a preliminary stage. Certainly the radiologist may or may not be able to detect these microcalcifications in the mammogram, MAMO2. If the radiologist detects them, another mammogram (say MAMO3) can be recommended after a month or so. By this time, she may have a more advanced stage of the cancer and develops not only a cluster of microcalcifications but also some masses like cysts in the breast. The radiologist after reading the mammogram, MAMO3, now recommends her for ultrasound scanning followed by biopsy. The phase of the Fourier spectrum of the mammogram in all three cases (MAMO1, MAMO2 and MAMO3) will be different and will often reflect only the changes in important features of the mammograms. However in the practical case, the random noise present in each mammogram may prevent reflection of actual changes in features of the two mammograms as random noise is also found in the high frequency components. This random noise is function of many parameters that can depend on the imaging system. Under preferred conditions, the amount of random noise in each mammogram may be more of less the same and cancel out when a comparison is drawn between these mammograms. Thus, when the high spatial frequencies due to subtle microcalcifications in MAMO2 are compared to high spatial frequencies in MAMO1, it more or less reflects the actual changes in important features (microcalcifications that are sign of precancerous tissue of the two mammograms). In the Fourier spectrum of MAMO3, the high spatial frequencies will increase due to the presence of clusters of microcalcifications and masses like cysts and/or tumors. A preferred embodiment of the present invention provides tracking of these changes in the important features of mammograms (MAMO1, MAMO2 and MAMO3) using the POC as well as spectral phase subtraction technique.

Figure 19B:
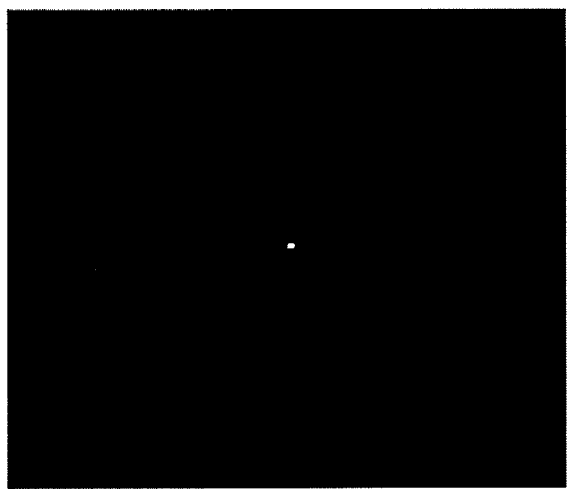
Figure 19C:
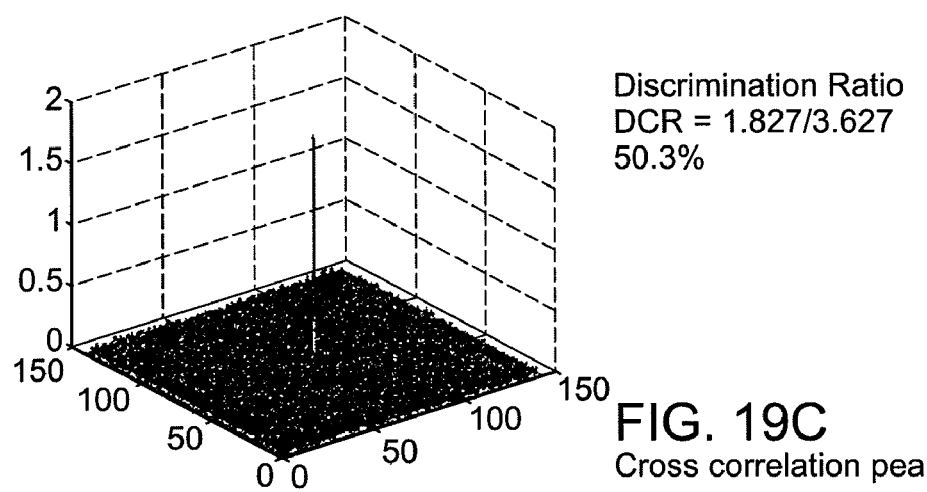
Figure 20:
FIG. 20 shows a phantom image with invisible micro calcification.
Figure 21:
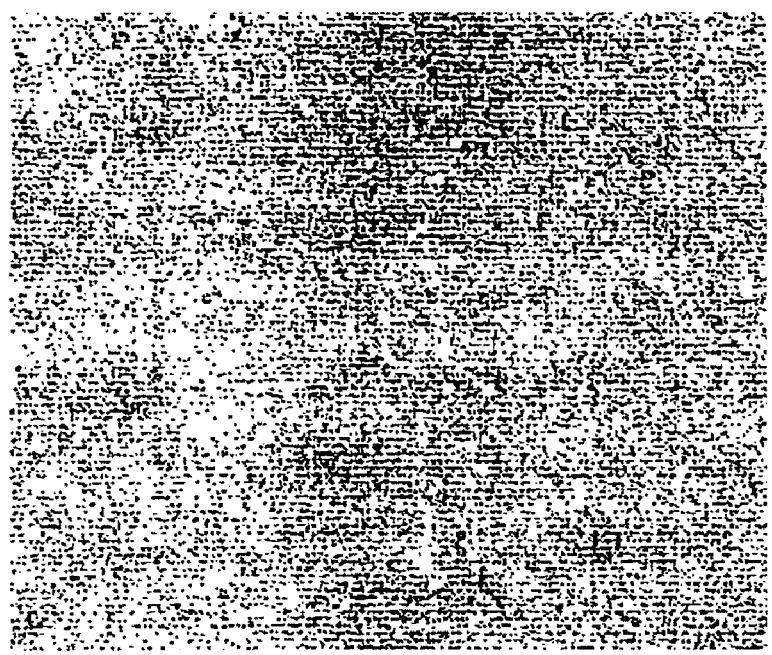
FIG. 21 shows a phantom image with invisible micro calcification.
Figure 22:
FIG. 22 shows a phantom image with invisible microcalcification.

The POC technique is analyzed with binary images as shown in FIG. 19A-19C and phantom images with invisible microcalcifications as shown in FIG. 20, FIG. 21 and FIG. 22. As discussed earlier these images, FIGS. 20-22, represent the stages of cancer over a period of time, MAMO1, MAMO2 and MAMO3 respectively. FIG. 20 consists of invisible bright random white spots that represent the random noise in the gray background that represents the soft dense tissue in the mammogram. In addition to these noise features of FIG. 20, FIG. 21 consists of an invisible cluster of bright spots with a definite pattern to represent the formation of microcalcifications at this state. Besides the noise features of FIG. 20 and represent microcalcifications of FIG. 21, FIG. 22 consists of features that resemble masses or cysts. This represents the advanced stage of cancer over a period of time.

If the reference image is same as the acquired image, the maximum value of the correlation peak that is obtained following the phase-only correlation (POC) method given in FIG. 17 is called the autocorrelation peak value. If the reference image and acquired image are different, then the maximum correlation peak value is called the cross correlation peak value.

The image in FIG. 20 can be used both as a reference as well as the acquired image to obtain the maximum autocorrelation peak value i.e. 3.3180. When the image in FIG. 20 is used as a reference and FIG. 21 as the acquired image, the maximum cross correlation peak value is 2.3734. Therefore the discrimination ratio is 0.7153. This indicates that there is 71.53% correlation between these two images. This correlation is due to only the important features of interest, i.e. high spatial frequencies (due to random noise) present in both the images as the background due to low frequencies are not included in the correlation method and are suppressed as phase-only information of the images is used in the correlation process. The 30 percent drop in the correlation is due to the cluster of simulated microcalcifications that are present in the image of FIG. 21.

When the image in FIG. 20 is used as a reference image and FIG. 22 as the acquired image the maximum cross correlation peak value is 1.5667. Therefore the discrimination ratio is 0.4722. This indicates that there is only 47.22% correlation between these two images. This correlation is due to only the essential features of interest, i.e. high spatial frequencies (due to random noise) present in both the images, as the background due to low frequencies are not included in the correlation method and are suppressed as phase-only information of the images is used in the correlation process. The 52.78% drop in the correlation is due to the cluster of simulated microcalcifications as well as masses or cysts that are present only in the image of FIG. 22.

Figure 23:
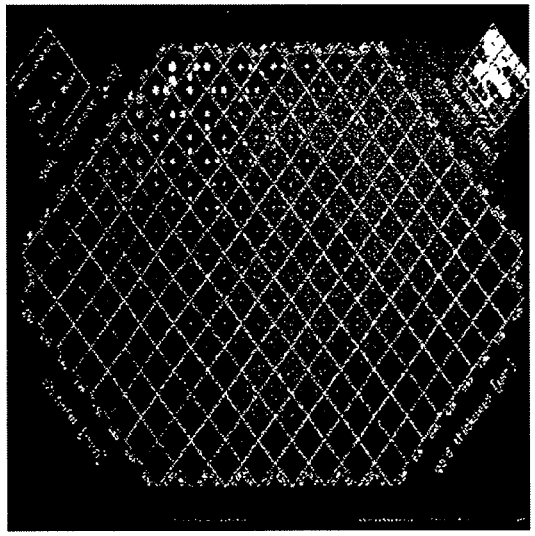
FIG. 23 shows a reference phantom image.
Figure 24:
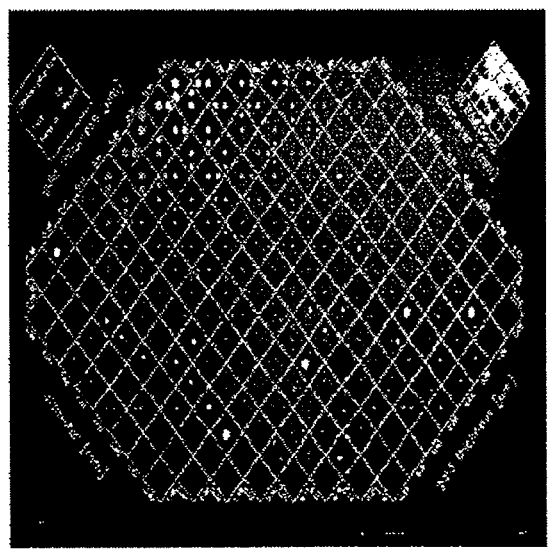
FIG. 24 shows a target image.
Figure 25:
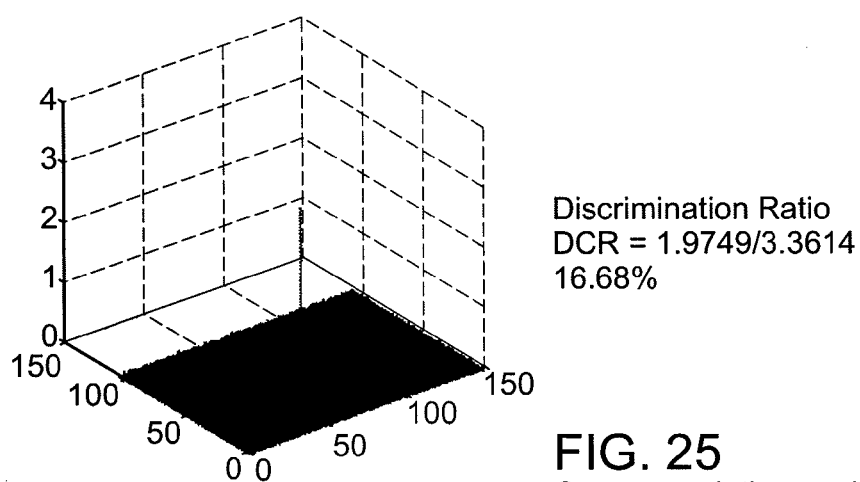
FIG. 25 shows a cross-correlation peak value.

The image in FIG. 21 is used both as both reference as well as a reference image to obtain the maximum autocorrelation peak value i.e. 3.3202. When the image in FIG. 21 is used as reference and FIG. 22 as the acquired image, the maximum cross correlation peak value is 1.7364. Therefore the discrimination ratio is 0.5230. This indicates that there is about 52.30% correlation between these two images. This correlation is due to only the essential features of interest, i.e. high spatial frequencies (due to cluster of simulated microcalcifications as well as random noise) present in both images as the background due to low frequencies are not included in the correlation method, and are suppressed as phase-only information of the images issued in the correlation process. The 48% drop in the correlation is due to the presence of masses or cysts that are present only in the image of FIG. 22. The image in FIG. 23 is used both as both reference as well as the acquired image to obtain the maximum autocorrelation peak value i.e. 3.3614. When the image in FIG. 23 is used as reference and FIG. 24 as the acquired image, the maximum cross correlation peal value is 0.5540. Therefore the discrimination ration is 0.1668. This tells us that there is only 17% correlation between these two images. This correlation is due to only the non important features of interest related to high spatial frequencies (due to the lines and letters that don't relate to the embedded gold particles) present in both the images as the background due to low frequencies are not included in the correlation method, and are suppresses as phase-only information of the images is used in the correlation process. The 83% drop in the correlation is due to addition of tiny bright spots to the image in FIG. 24.

Figure 26:
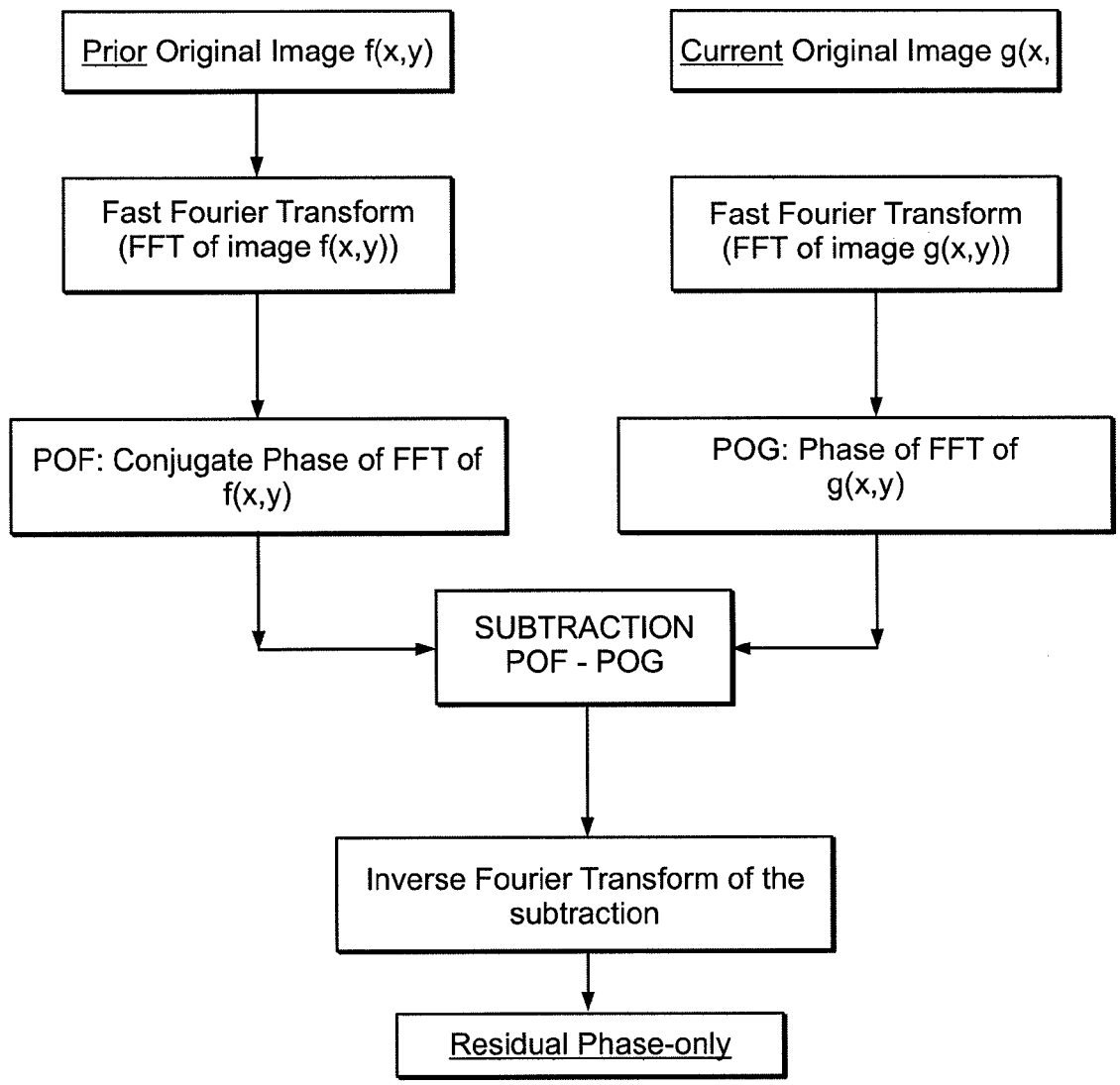
FIG. 26 illustrates a process sequence in accordance with a preferred embodiment of the invention.

A process sequence for spectral phase subtraction is shown in FIG. 26. Since the phase of the Fourier transform contains the important features of an image, the changes in the feature of subsequent images obtained over a period of time can be tracked using this technique. The phase-only information of prior image is subtracted from the phase-only information of the current image. This residual information is inverse Fourier transformed to reconstruct the residual image. Our results show that these residual images clearly display only the changes in the important features (high spatial frequencies) between these two images.

The residual phase-only image shown in FIG. 29A is obtained by subtracting phase-only information of FIG. 20 from phase-only information of FIG. 21 following the method given in FIG. 26. This residual image clearly shows only the changes in the important features, i.e., changes in high spatial frequencies, (cluster of simulated microcalcifications) between these images. The background present in two images is suppressed because we used both images canceled out during the subtraction process.

The residual phase-only image shown in FIG. 29B is obtained by subtracting phase-only information of FIG. 20 from phase-only information of FIG. 22 following the method given in FIG. 26. This residual image clearly shows only the changes in the important features, i.e. changes in high spatial frequencies, (cluster of simulated microcalcifications and masses with their shape and edge) between these images. The background present in two images is suppressed because we used phase-only information for subtraction, while high spatial frequency component due to random noise that is present in both images canceled out during the subtraction process.

The residual phase-only image shown in FIG. 29C is obtained by subtracting phase-only information of FIG. 21 from phase-only information of FIG. 22 following the method given in FIG. 26. This residual image clearly shows only the changes in the important features, i.e. changes in high spatial frequencies, (masses with their shape and edge) between these images. The background present in two images is suppressed because we used phase-only information for subtraction, while high spatial frequency features due to random noise as well as cluster of simulated microcalcifications that are present in both the images canceled out during the subtraction process.

What is claimed is:

1. A method for analyzing images of a region of interest comprising:
   providing a digital image of the region of interest;
   processing the digital image using a digital image processor to Fourier transform the digital image;
   extracting spectral phase information from the Fourier transformed digital image;
   multiplying the spectral phase information by a spectral amplitude; and
   performing an inverse Fourier transform on the multiplied spectral phase information to generate an enhanced digital image, wherein the enhanced digital image provides a greater level of contrast than the digital image.

2. The method of claim 1 further comprising performing a fast Fourier transform on the digital image.

3. The method of claim 1 wherein the images are selected from the group consisting of a mammographic image, an image of obstructions within a coronary artery, an image of a kidney, an image of a bone, and an image of a spinal column.

4. The method of claim 1 further comprising acquiring a plurality of different images of the region of interest at different times and comparing the different images.

5. The method of claim 4 further comprising subtracting a first spectral phase information from a second spectral phase information.

6. The method of claim 1 further comprising identifying calcified material in the spectral phase information.

7. The method of claim 1 further comprising detecting a precancerous or cancerous lesion from the spectral phase information.

8. The method of claim 1 further comprising providing a plurality of reference images having known signal characteristics.

9. The method of claim 1, wherein the amplitude data comprises a unit magnitude.

10. The method of claim 1, wherein the amplitude data comprises averaged spectral amplitude data.

11. The method of claim 10, wherein the average amplitude comprises an average of spectral amplitude data from a plurality of Fourier transformed digital images.

12. The method of claim 10, wherein the average spectral amplitude includes spectral amplitude data from said digital image.

13. A medical imaging system comprising:
   an x-ray source;
   an imaging detector configured to detect x-ray radiation to create a digital image;
   a processor having a program to process the image from the imaging detector, the processor containing logic to perform the following processing functions:
   Fourier transforming the digital image;
   extracting spectral phase information from the Fourier transformed digital image;
   multiplying the spectral phase information by a spectral amplitude; and
   performing an inverse Fourier transform on the multiplied spectral phase information to generate an enhanced digital image, wherein the enhanced digital image provides a greater level of contrast than the digital image.

14. The imaging system of claim 13 wherein the processor separates phase and amplitude information from the Fourier transformed digital image.

15. The imaging system of claim 13 wherein the detector is selected from a group comprising a charge-coupled device, a CMOS imaging sensor or an amorphous silicon imaging detector.

16. The imaging system of claim 13 further comprising a patient support that positions a patient relative to the imaging detector.

17. The imaging system of claim 13 wherein the system comprises a full field digital mammography imaging device.

18. The imaging system of claim 13 wherein the system comprises a computed tomography imaging system.

19. The imaging system of claim 13 further comprising a computer having an image processor, a memory, a display and a user interface.

20. The system of claim 13, wherein the amplitude data comprises a unit magnitude.

21. The system of claim 13, wherein the amplitude data comprises averaged spectral amplitude data.

22. The system of claim 21, wherein the average amplitude comprises an average of spectral amplitude data from a plurality of Fourier transformed digital images.

23. The system of claim 21, wherein the average spectral amplitude includes spectral amplitude data from said digital image.

24. A method of analyzing mammograms comprising:
   providing a digital mammogram;
   processing the digital mammogram using a digital processor to Fourier transform the digital mammogram;
   extracting spectral phase information from the Fourier transformed digital mammogram;
   multiplying the spectral phase information by a spectral amplitude; and
   performing an inverse Fourier transform on the multiplied spectral phase information to generate an enhanced digital image, wherein the enhanced digital mammogram provides a greater level of contrast than the digital mammogram.

* * * * *

UNITED STATES PATENT AND TRADEMARK OFFICE
CERTIFICATE OF CORRECTION

PATENT NO. : 7,653,232 B2 Page 1 of 1
APPLICATION NO. : 11/342254
DATED : January 26, 2010
INVENTOR(S) : Kothapalli et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 827 days.

Signed and Sealed this

Twenty-eighth Day of December, 2010

David J. Kappos
*Director of the United States Patent and Trademark Office*